(12) United States Patent
McDonald et al.

(10) Patent No.: US 8,585,606 B2
(45) Date of Patent: Nov. 19, 2013

(54) PHYSIOLOGICAL STATUS MONITORING SYSTEM

(75) Inventors: David McDonald, Medway, MA (US); Craig D. Mielcarz, Somerville, MA (US); Sergey Nikiforenko, Ayer, MA (US); Vernon A. Gambetta, Sarasota, FL (US)

(73) Assignee: Qinetiq North America, Inc., Reston, VA (US)

( * ) Notice: Subject to any disclaimer, the term of this patent is extended or adjusted under 35 U.S.C. 154(b) by 313 days.

(21) Appl. No.: 12/924,241

(22) Filed: Sep. 23, 2010

(65) Prior Publication Data
US 2012/0078127 A1 Mar. 29, 2012

(51) Int. Cl.
*A61B 5/0205* (2006.01)
(52) U.S. Cl.
USPC .......................................... 600/508
(58) Field of Classification Search
USPC ........... 600/300–301, 483–484, 508; 482/1–9
See application file for complete search history.

(56) References Cited

U.S. PATENT DOCUMENTS

| | | | |
|---|---|---|---|
| 2,021,111 A | 11/1935 | Wheat | |
| 2,953,970 A | 9/1960 | Maynard | |
| 2,963,535 A | 12/1960 | Wegener et al. | |
| 2,963,538 A | 12/1960 | Dahlgren | |
| 2,997,521 A | 8/1961 | Dahlgren | |
| 3,086,071 A | 4/1963 | Preston | |
| 3,229,030 A | 1/1966 | Baermann | |
| 3,247,755 A | 4/1966 | Siegmund | |
| 3,288,175 A | 11/1966 | Valko | |
| 3,371,250 A | 2/1968 | Ross et al. | |
| 3,414,666 A | 12/1968 | Doundoulakis et al. | |
| 3,447,120 A | 5/1969 | Rask et al. | |

(Continued)

FOREIGN PATENT DOCUMENTS

DE  103 06 953 A1  10/2003
EP  0320901 A2  6/1989

(Continued)

OTHER PUBLICATIONS

Axisa, F. et al,; "Flexible Technologies and Smart Clothing for Citizen, Medicine, Home Healthcare, and Disease Prevention", IEEE transactions on Information Technology in Biomedicine, vol. 9, No. 3, Sep. 2005, p. 325-336.

(Continued)

Primary Examiner — Amanda Patton
(74) Attorney, Agent, or Firm — Iandiorio Teska & Coleman, LLP

(57) ABSTRACT

A load score system includes a metabolic sensor such as a heart rate sensor for a subject is configured to output metabolic data for the subject. A biomechanical load sensing subsystem for the subject is configured to output biomechanical load data. A speed sensor subsystem for the subject is configured to output speed data. One or more databases store zones and a weighting factor for each zone for metabolic data, biomechanical load data, and speed data. A performance module is responsive to the metabolic data, the biomechanical load data, and the speed data and the one or more databases and is configured to calculate a metabolic load score for the subject. A biomechanical load score for the subject and a speed load score for the subject are also calculated. An output module displays the subject's calculated metabolic, biomechanical, and speed load scores.

27 Claims, 16 Drawing Sheets

(56) References Cited

U.S. PATENT DOCUMENTS

| | | |
|---|---|---|
| 3,473,872 A | 10/1969 | Okamura |
| 3,476,870 A | 11/1969 | Ross |
| 3,479,565 A | 11/1969 | Ross et al. |
| 3,495,025 A | 2/1970 | Ross |
| 3,507,321 A | 4/1970 | Palma |
| 3,551,585 A | 12/1970 | Smart et al. |
| 3,627,903 A | 12/1971 | Plummer |
| 3,631,298 A | 12/1971 | Davis |
| 3,654,380 A | 4/1972 | Tatum et al. |
| 3,700,538 A | 10/1972 | Kennedy |
| 3,711,627 A | 1/1973 | Maringulov |
| 3,778,331 A | 12/1973 | Scharf |
| 3,878,316 A | 4/1975 | Groff |
| 3,882,846 A | 5/1975 | Fletcher et al. |
| 3,891,011 A | 6/1975 | Tisdale et al. |
| 3,909,508 A | 9/1975 | Ross |
| 3,926,360 A | 12/1975 | Moister, Jr. |
| 3,984,622 A | 10/1976 | Ross |
| 4,031,284 A | 6/1977 | Ingraham |
| 4,034,150 A | 7/1977 | Burnett, III |
| 4,035,694 A | 7/1977 | Barton et al. |
| 4,095,042 A | 6/1978 | Ross |
| 4,103,102 A | 7/1978 | Klein |
| 4,106,677 A | 8/1978 | Helmso et al. |
| 4,111,510 A | 9/1978 | Zurcher |
| 4,143,236 A | 3/1979 | Ross et al. |
| 4,145,030 A | 3/1979 | Ingraham |
| 4,150,464 A | 4/1979 | Tracy |
| 4,158,103 A | 6/1979 | Danilin et al. |
| 4,158,104 A | 6/1979 | Ross |
| 4,159,394 A | 6/1979 | Ross |
| 4,171,555 A | 10/1979 | Bakker et al. |
| 4,191,800 A | 3/1980 | Holtzman |
| 4,196,355 A | 4/1980 | Maine |
| 4,227,520 A | 10/1980 | Lord |
| 4,229,615 A | 10/1980 | Orr, Jr. et al. |
| 4,249,267 A | 2/1981 | Voss |
| 4,254,951 A | 3/1981 | De Laney |
| 4,281,211 A | 7/1981 | Tatum et al. |
| 4,281,237 A | 7/1981 | Berenson |
| 4,370,658 A | 1/1983 | Hill |
| 4,373,534 A | 2/1983 | Watson |
| 4,430,384 A | 2/1984 | George |
| 4,442,314 A | 4/1984 | Piper |
| 4,452,847 A | 6/1984 | Siemon |
| 4,460,803 A | 7/1984 | Piper |
| 4,463,323 A | 7/1984 | Piper |
| 4,504,696 A | 3/1985 | Piper |
| 4,513,055 A | 4/1985 | Leibowitz |
| 4,527,135 A | 7/1985 | Piper |
| 4,550,411 A | 10/1985 | Stonestreet et al. |
| 4,559,411 A | 12/1985 | Piper |
| 4,572,197 A | 2/1986 | Moore et al. |
| 4,590,623 A | 5/1986 | Kitchman |
| 4,658,089 A | 4/1987 | Guzy et al. |
| 4,670,351 A | 6/1987 | Keane et al. |
| 4,682,828 A | 7/1987 | Piper et al. |
| 4,684,762 A | 8/1987 | Gladfelter |
| 4,709,397 A | 11/1987 | Voshall et al. |
| 4,712,298 A | 12/1987 | Mondor, III |
| 4,723,925 A | 2/1988 | Orr, Jr. et al. |
| 4,735,847 A | 4/1988 | Fujiwara et al. |
| 4,741,707 A | 5/1988 | Mondor, III |
| 4,746,769 A | 5/1988 | Piper |
| 4,753,088 A | 6/1988 | Harrison et al. |
| 4,761,005 A | 8/1988 | French et al. |
| 4,774,434 A | 9/1988 | Bennion |
| 4,784,162 A | 11/1988 | Ricks et al. |
| 4,803,096 A | 2/1989 | Kuhn et al. |
| 4,804,806 A | 2/1989 | Orr, Jr. et al. |
| 4,807,640 A | 2/1989 | Watson et al. |
| 4,808,771 A | 2/1989 | Orr, Jr. et al. |
| 4,814,585 A | 3/1989 | Klein |
| 4,815,473 A | 3/1989 | Watson et al. |
| 4,817,625 A | 4/1989 | Miles |
| 4,827,943 A | 5/1989 | Bornn et al. |
| 4,851,613 A | 7/1989 | Jacques |
| 4,854,446 A | 8/1989 | Strader |
| 4,856,837 A | 8/1989 | Hammersla, Jr. |
| 4,868,565 A | 9/1989 | Mettes et al. |
| 4,875,144 A | 10/1989 | Wainwright |
| 4,877,646 A | 10/1989 | Kuhn et al. |
| 4,910,358 A | 3/1990 | Mittelbusher |
| 4,912,611 A | 3/1990 | Lyle |
| 4,913,978 A | 4/1990 | Klotz et al. |
| 4,930,517 A | 6/1990 | Cohen et al. |
| 4,948,951 A | 8/1990 | Balzano |
| 4,960,118 A | 10/1990 | Pennock |
| 4,983,452 A | 1/1991 | Daimon et al. |
| 4,992,335 A | 2/1991 | Guerra et al. |
| 5,008,517 A | 4/1991 | Brekkestran et al. |
| 5,032,705 A | 7/1991 | Batcheller et al. |
| 5,047,788 A | 9/1991 | Gillard |
| 5,073,984 A | 12/1991 | Tone et al. |
| 5,076,801 A | 12/1991 | Schroll |
| 5,089,669 A | 2/1992 | Piper et al. |
| 5,095,628 A | 3/1992 | McKenney et al. |
| 5,103,504 A | 4/1992 | Dordevic |
| 5,104,726 A | 4/1992 | Ross |
| 5,119,020 A | 6/1992 | Massey et al. |
| 5,126,920 A | 6/1992 | Cardashian et al. |
| 5,140,131 A | 8/1992 | Macher et al. |
| 5,191,893 A | 3/1993 | Reiten |
| 5,203,717 A | 4/1993 | Beck et al. |
| 5,216,732 A | 6/1993 | Knott |
| 5,241,300 A | 8/1993 | Buschmann |
| 5,259,792 A | 11/1993 | Beck et al. |
| 5,277,617 A | 1/1994 | Shasteen |
| 5,295,490 A | 3/1994 | Dodakian |
| 5,301,678 A | 4/1994 | Watson et al. |
| 5,316,830 A | 5/1994 | Adams, Jr. et al. |
| 5,318,845 A | 6/1994 | Tanaka et al. |
| 5,331,115 A | 7/1994 | Ysbrand |
| 5,332,869 A | 7/1994 | Hagiwara |
| 5,342,204 A | 8/1994 | Och |
| 5,348,008 A | 9/1994 | Bornn et al. |
| 5,353,793 A | 10/1994 | Bornn |
| 5,357,593 A | 10/1994 | Bossler |
| 5,362,656 A | 11/1994 | McMahon |
| 5,371,326 A | 12/1994 | Clearwaters-Dreager et al. |
| 5,373,103 A | 12/1994 | Orr, Jr. et al. |
| 5,380,954 A | 1/1995 | Orr, Jr. |
| 5,387,113 A | 2/1995 | Dickerson et al. |
| 5,393,928 A | 2/1995 | Cribb et al. |
| 5,415,561 A | 5/1995 | Mavrin et al. |
| 5,416,310 A | 5/1995 | Little |
| 5,457,610 A | 10/1995 | Bernardoni et al. |
| 5,499,927 A | 3/1996 | Ohno et al. |
| 5,502,631 A | 3/1996 | Adachi |
| 5,523,528 A | 6/1996 | Bese et al. |
| 5,531,405 A | 7/1996 | Goldberg |
| 5,532,429 A | 7/1996 | Dickerson et al. |
| 5,538,781 A | 7/1996 | Rao et al. |
| 5,543,585 A | 8/1996 | Booth et al. |
| 5,600,098 A | 2/1997 | Kazaks |
| 5,674,752 A | 10/1997 | Buckley et al. |
| 5,680,681 A | 10/1997 | Fuss |
| 5,691,062 A | 11/1997 | Shalaby et al. |
| 5,701,370 A | 12/1997 | Muhs et al. |
| 5,730,145 A | 3/1998 | Defares et al. |
| 5,747,101 A | 5/1998 | Booth et al. |
| 5,749,365 A | 5/1998 | Magill |
| 5,760,340 A | 6/1998 | Orr, Jr. et al. |
| 5,763,058 A | 6/1998 | Isen et al. |
| 5,769,755 A | 6/1998 | Henry et al. |
| 5,773,762 A | 6/1998 | Orr, Jr. et al. |
| 5,774,341 A | 6/1998 | Urbish et al. |
| 5,786,977 A | 7/1998 | Cohen |
| 5,788,528 A | 8/1998 | Orr, Jr. et al. |
| 5,798,907 A | 8/1998 | Janik |
| 5,802,607 A | 9/1998 | Triplette |
| 5,824,996 A | 10/1998 | Kochman et al. |
| 5,829,987 A | 11/1998 | Fritsch et al. |
| 5,831,198 A | 11/1998 | Turley et al. |

(56) References Cited

U.S. PATENT DOCUMENTS

| | | |
|---|---|---|
| 5,832,296 A | 11/1998 | Wang et al. |
| 5,834,693 A | 11/1998 | Waddell et al. |
| 5,837,624 A | 11/1998 | Sakaguchi et al. |
| 5,876,430 A | 3/1999 | Shoberg et al. |
| 5,883,364 A | 3/1999 | Frei et al. |
| 5,906,004 A | 5/1999 | Lebby et al. |
| 5,911,595 A | 6/1999 | Orr, Jr. et al. |
| 5,912,653 A | 6/1999 | Fitch |
| 5,913,830 A | 6/1999 | Miles |
| 5,914,585 A | 6/1999 | Grabon |
| 5,914,660 A | 6/1999 | Mesibov et al. |
| 5,919,141 A | 7/1999 | Money et al. |
| 5,926,144 A | 7/1999 | Bolanos et al. |
| 5,928,157 A | 7/1999 | O'Dwyer |
| 5,931,764 A | 8/1999 | Freeman et al. |
| 5,970,921 A | 10/1999 | Fulton |
| 5,989,120 A | 11/1999 | Truchsess |
| 5,995,077 A | 11/1999 | Wilcox et al. |
| 5,997,983 A | 12/1999 | Caron et al. |
| 6,023,372 A | 2/2000 | Spitzer et al. |
| 6,024,575 A | 2/2000 | Ulrich |
| 6,026,512 A | 2/2000 | Banks |
| 6,047,203 A | 4/2000 | Sackner et al. |
| 6,080,690 A | 6/2000 | Lebby et al. |
| 6,083,156 A | 7/2000 | Lisiecki |
| 6,097,607 A | 8/2000 | Carroll et al. |
| 6,105,624 A | 8/2000 | Wildeman et al. |
| 6,117,554 A | 9/2000 | Shalaby et al. |
| 6,121,171 A | 9/2000 | Takahashi et al. |
| 6,121,547 A | 9/2000 | Harada |
| 6,126,572 A | 10/2000 | Smith |
| 6,128,004 A | 10/2000 | McDowall et al. |
| 6,135,951 A * | 10/2000 | Richardson et al. .......... 600/300 |
| 6,137,675 A | 10/2000 | Perkins |
| 6,145,551 A | 11/2000 | Jayaraman et al. |
| 6,210,771 B1 | 4/2001 | Post et al. |
| 6,231,516 B1 | 5/2001 | Keilman et al. |
| 6,253,099 B1 | 6/2001 | Oskin et al. |
| 6,254,548 B1 | 7/2001 | Ishikawa et al. |
| 6,254,551 B1 | 7/2001 | Varis |
| 6,270,466 B1 | 8/2001 | Weinstein et al. |
| 6,277,080 B1 | 8/2001 | Nissila et al. |
| 6,295,466 B1 | 9/2001 | Ishikawa et al. |
| 6,306,088 B1 | 10/2001 | Krausman et al. |
| 6,315,009 B1 | 11/2001 | Jayaraman et al. |
| 6,319,015 B1 | 11/2001 | Faunce |
| 6,324,053 B1 | 11/2001 | Kamijo |
| 6,325,066 B1 | 12/2001 | Hughes et al. |
| 6,341,504 B1 | 1/2002 | Istook |
| 6,341,550 B1 | 1/2002 | White |
| 6,350,129 B1 | 2/2002 | Gorlick |
| 6,381,482 B1 | 4/2002 | Jayaraman et al. |
| 6,385,473 B1 | 5/2002 | Haines et al. |
| 6,413,225 B1 | 7/2002 | Sackner et al. |
| 6,416,471 B1 | 7/2002 | Kumar et al. |
| 6,420,008 B1 | 7/2002 | Lewis et al. |
| 6,445,940 B1 | 9/2002 | Gevins et al. |
| 6,461,307 B1 | 10/2002 | Kristbjarnarson et al. |
| 6,463,310 B1 | 10/2002 | Swedlow et al. |
| 6,474,367 B1 | 11/2002 | Jayaraman et al. |
| 6,493,933 B1 | 12/2002 | Post et al. |
| 6,494,829 B1 | 12/2002 | New, Jr. et al. |
| 6,496,695 B1 | 12/2002 | Kouji et al. |
| 6,522,531 B1 | 2/2003 | Quintana et al. |
| 6,527,711 B1 | 3/2003 | Stivoric et al. |
| 6,551,252 B2 | 4/2003 | Sackner et al. |
| 6,561,987 B2 | 5/2003 | Pail |
| 6,677,858 B1 | 1/2004 | Faris et al. |
| 6,687,523 B1 | 2/2004 | Jayaramen et al. |
| 6,727,197 B1 | 4/2004 | Wilson et al. |
| 6,729,025 B2 | 5/2004 | Farrell et al. |
| 6,743,030 B2 | 6/2004 | Lin et al. |
| 6,767,218 B2 | 7/2004 | Marmaropoulos |
| 6,783,498 B2 | 8/2004 | Sackner et al. |
| 6,785,144 B1 | 8/2004 | Akram |
| 6,854,988 B2 | 2/2005 | Marmaropoulos et al. |
| 6,895,261 B1 | 5/2005 | Palamides |
| 6,936,011 B2 | 8/2005 | Sheldon |
| 6,941,775 B2 | 9/2005 | Sharma |
| 6,970,731 B1 | 11/2005 | Jayaraman et al. |
| 7,020,508 B2 * | 3/2006 | Stivoric et al. ............... 600/390 |
| 7,041,062 B2 | 5/2006 | Friedrichs et al. |
| 7,076,291 B2 | 7/2006 | Pulkkinen et al. |
| 7,092,846 B2 | 8/2006 | Vock et al. |
| 7,265,970 B2 | 9/2007 | Jordan |
| 7,319,895 B2 | 1/2008 | Klefstad-Sillonville et al. |
| 7,559,902 B2 | 7/2009 | Ting et al. |
| 7,618,260 B2 | 11/2009 | Daniel et al. |
| 7,731,517 B2 | 6/2010 | Lee et al. |
| 7,878,030 B2 | 2/2011 | Burr |
| 7,881,051 B2 | 2/2011 | Kim |
| 7,980,867 B2 | 7/2011 | Dei Rossi et al. |
| 8,029,300 B2 | 10/2011 | Finney et al. |
| 8,086,421 B2 * | 12/2011 | Case et al. ..................... 702/182 |
| 8,200,323 B2 * | 6/2012 | DiBenedetto et al. ........ 600/519 |
| 2002/0032388 A1 | 3/2002 | Kristbjarnarson et al. |
| 2002/0044059 A1 | 4/2002 | Reeder et al. |
| 2002/0107451 A1 | 8/2002 | Pulkkinen et al. |
| 2002/0124295 A1 | 9/2002 | Fenwick et al. |
| 2003/0139680 A1 | 7/2003 | Sheldon |
| 2004/0092186 A1 | 5/2004 | Wilson-Nguyen et al. |
| 2004/0097823 A1 | 5/2004 | Friedrichs et al. |
| 2004/0209396 A1 | 10/2004 | Krulevitch et al. |
| 2004/0224138 A1 | 11/2004 | Farrell et al. |
| 2004/0225199 A1 | 11/2004 | Evanyk et al. |
| 2005/0054941 A1 | 3/2005 | Ting et al. |
| 2005/0119586 A1 | 6/2005 | Coyle et al. |
| 2005/0227811 A1 | 10/2005 | Shum et al. |
| 2005/0240087 A1 | 10/2005 | Keenan et al. |
| 2006/0009697 A1 | 1/2006 | Banet et al. |
| 2006/0036142 A1 | 2/2006 | Brister et al. |
| 2006/0117805 A1 | 6/2006 | Valentine et al. |
| 2007/0105404 A1 | 5/2007 | Lee et al. |
| 2007/0115259 A1 | 5/2007 | Pai |
| 2007/0118043 A1 | 5/2007 | Oliver et al. |
| 2007/0279852 A1 | 12/2007 | Daniel et al. |
| 2007/0299325 A1 | 12/2007 | Farrell et al. |
| 2008/0000304 A1 | 1/2008 | Nagle et al. |
| 2008/0015454 A1 | 1/2008 | Gal |
| 2008/0139894 A1 | 6/2008 | Szydlo-Moore et al. |
| 2008/0188353 A1 * | 8/2008 | Vitolo et al. ...................... 482/8 |
| 2008/0191106 A1 | 8/2008 | Shiffler et al. |
| 2009/0131759 A1 | 5/2009 | Sims et al. |
| 2009/0190713 A1 | 7/2009 | Wai |
| 2011/0251469 A1 | 10/2011 | Varadan |
| 2011/0275940 A1 | 11/2011 | Nims et al. |
| 2011/0295083 A1 | 12/2011 | Doelling et al. |

FOREIGN PATENT DOCUMENTS

| | | |
|---|---|---|
| EP | 1 064 963 A1 | 1/2001 |
| EP | 1 077 044 A1 | 2/2001 |
| EP | 1 164 815 A1 | 12/2001 |
| EP | 1 234 903 A1 | 8/2002 |
| EP | 1 328 137 A2 | 7/2003 |
| EP | 1 330 964 A2 | 7/2003 |
| EP | 1 339 259 A1 | 8/2003 |
| EP | 1 444 907 A1 | 8/2004 |
| EP | 1 269 502 B1 | 6/2005 |
| EP | 1 021 064 B1 | 9/2005 |
| EP | 1 049 354 B1 | 12/2005 |
| EP | 1 201 806 B1 | 12/2005 |
| FR | 2 836 050 A1 | 2/2003 |
| FR | 2858758 A2 | 8/2003 |
| GB | 2 143 135 A | 2/1985 |
| GB | 2 331 631 A | 2/1999 |
| GB | 2 336 514 A | 10/1999 |
| GB | 2 378 054 A | 1/2003 |
| GB | 2 385 277 A | 8/2003 |
| GB | 2 386 339 A | 9/2003 |
| GB | 2 396 256 A | 6/2004 |
| WO | WO 98/20200 | 5/1998 |
| WO | WO 99/19019 | 4/1999 |
| WO | WO 99/64657 | 12/1999 |

(56) References Cited

FOREIGN PATENT DOCUMENTS

| WO | WO 00/025193 | | 5/2000 |
|---|---|---|---|
| WO | WO 01/78577 | A2 | 10/2001 |
| WO | WO 01/88935 | | 11/2001 |
| WO | WO 02/07816 | | 1/2002 |
| WO | WO 02/045538 | A2 | 6/2002 |
| WO | WO 02/060370 | A2 | 8/2002 |
| WO | WO 02/087929 | A1 | 11/2002 |
| WO | WO 02/095839 | A2 | 11/2002 |
| WO | WO 03/039417 | A2 | 5/2003 |
| WO | WO 03/052541 | A2 | 6/2003 |
| WO | WO 03/072861 | A1 | 9/2003 |
| WO | WO 03/094717 | A1 | 11/2003 |
| WO | WO 2004/053638 | A2 | 6/2004 |
| WO | WO 2004/064108 | A2 | 7/2004 |
| WO | WO 2004/091503 | A2 | 10/2004 |
| WO | WO 2004/098703 | A2 | 11/2004 |
| WO | WO 2004/107831 | A2 | 12/2004 |
| WO | WO 2004/114401 | A2 | 12/2004 |
| WO | WO 2005/000052 | A1 | 1/2005 |
| WO | WO 2005/011415 | A1 | 2/2005 |
| WO | WO 2005/013738 | A2 | 2/2005 |
| WO | WO 2008039082 | | 4/2008 |

OTHER PUBLICATIONS

Pandian, P.S. et al.; "Wireless Sensor Network for Wearable Physiological Monitoring",; Journal of Networks, vol. 3, No. 5, May 2008, p. 21-29.

Shaw, G. A. et al.; "Warfighter Physiological and Environmental Monitoring: A Study for the U.S. Army Research Institute in Environmental Medicine and the Soldier Systems Center", Lincoln Laboratory, MIT, Nov. 2004, (141 total pages (as available)).

Mathews, R. et al.; "Wearable Physiological Sensor Suite for Unobtrusive Monitoring of Physiological and Cognitive State", Proceedings of the 29th Annual International Conference of the IEEE EMBS Cité Internationale, Lyon, France, Aug. 23-26, 2007, six (6) pages total.

U.S. Appl. No. 12/799,822, filed Nov. 3, 2011 (projected), Richard B. Streeter.

U.S. Appl. No. 12/804,761, filed Feb. 20, 2010 (projected), DeRemer et al.

U.S. Appl. No. 12/804,962, filed Feb. 9, 2012 (projected), Mielcarz et al.

Gemperie, Francine, Kasabach, Chris, Stivoric, John, Bauer, Malcolm and Martin, Richard, *Design for Wearability*, Institute for Complex Engineered Systems, Carnegie Mellon University, Pittsburgh, PA http://www.ices.emu.edu/design/weability, 1998 (7 pages).

"E-broidery: Design and Fabrication of Textile-based Computing", by E.R. Post et al., IBM Systems Journal, vol. 39, Nos. 3 & 4, 2000, pp. 840-860.

"Intrabody Buses for Data and Power", E. Rhemi Post et al., MIT Media Laboratory, 1997 IEEE, pp. 52-55.

Landon, Chris, Respiratory Monitoring: Advantages of Inductive Plethysmography over Impedance Pneumography, a whitepaper published by VivoMetrics, date unknown, pp. 1-7.

E. Rehmi Post and Maggie Orth, Smart Fabric, or "Wearable Clothing", the MIT Media Laboratory, pp. 167-168 of the Digest of Papers of the First IEEE International Symposium on Wearable Computers, Oct. 13-14, 1997 held in Cambridge, Massachusetts.

"Wearable Sensor Badge & Sensor Jacket for Context Awareneess", Farringdon et al., Philips Research Laboratories, Surrey, U.K., 1999, IEEE pp. 107-113.

"Electronic Suspenders: A Fabric Power bus and Data Network for Wearable Digital Devices", Michael M. Gorlick, The Aerospace Corporation, El Segundo, California, 1999, IEEE, pp. 114-121.

Harper, Charles A., Handbook of Plastics, Elastomers, and Composites, Third Edition, McGraw-Hill, New York, 1996, pp. 6.14-6.19 (4 pages).

Neuman, Michael R., Biopotential Electrodes. The Biomedical Engineering Handbook, vol. 1, edited by Joseph D. Bronzino, CRC Press, Boca Raton, FL, 2000, pp. 48-1-48-12.

Post, E. Rhemi and Maggie Orth, Smart Fabric, or Washable Computing, the MIT Media Laboratory, Digest of Papers of the first IEEE International Symposium on Wearable Computers, Oct. 13-14, 1997 held in Cambridge, Massachusetts (4 pages).

Zephyr Biotechnology, Zephyr BioHarness, www.zephyrtechnology.com (2 pages).

* cited by examiner

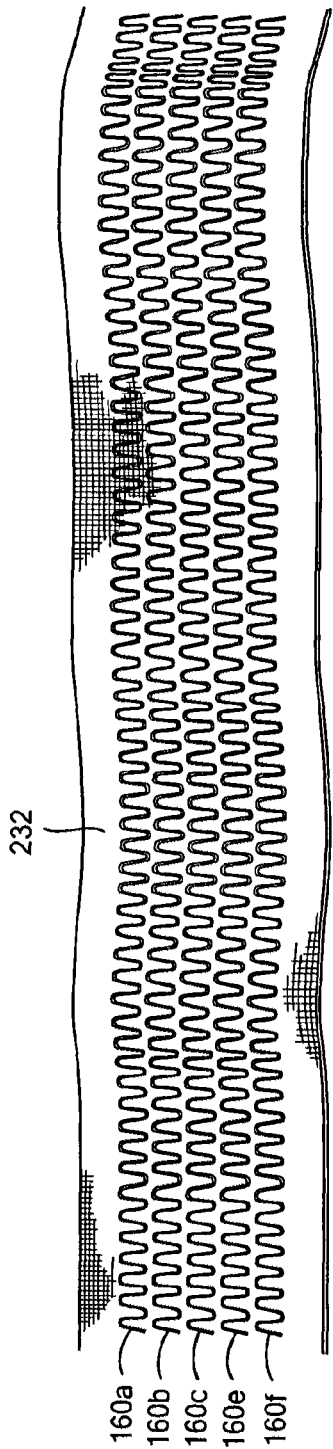
FIG. 14
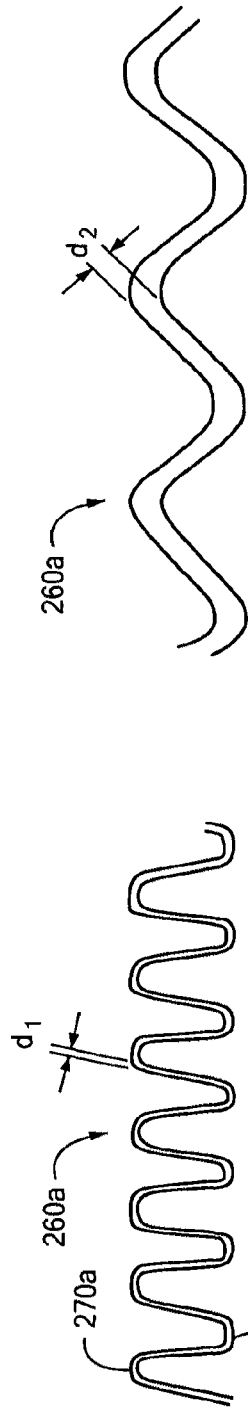
FIG. 15A
FIG. 15B

PHYSIOLOGICAL STATUS MONITORING SYSTEM

FIELD OF THE INVENTION

The subject invention relates to physiological monitoring systems.

BACKGROUND OF THE INVENTION

Various physiological monitoring systems have been proposed. Some determine only speed and distance. Others monitor the heart rate, respiration rate, and the like of an athlete, soldier, or first responder. Polar U.S.A., offers a Team[2] product in which athletes wear a chest strap equipped with a heart rate monitor and a transmitter which transmits heart rate data to a wristwatch worn by each athlete and also to a base station connected to a personal computer monitored by a coach and/or trainer. It is also known to display a person's heart rate and to relate the heart rate to minimums, maximums, percentages of the maximum, and the like. See, for example, U.S. Pat. No. 7,076,291 incorporated herein by this reference. Zones (e.g., maximum, performance, fat burning, warm up, and the like) are also known, and they are typically based on percentages of a person's maximum heart rate. See, for example, U.S. Pat. No. 5,769,755 incorporated herein by this reference.

BRIEF SUMMARY OF THE INVENTION

Coaches and trainers, as discovered by the applicant hereof, are most desirous of knowing their athletes heart rate and speed and also the biomechanical load experienced by each athlete. In a given workout, two athletes may raise their heart rates to about the same level but one athlete may be working harder than the other because he is moving faster and/or is experiencing higher loads.

Thus, heart rate data alone may not tell the whole story. The subject invention provides a novel method of providing coaches and trainers with the data they desire most. A new physiological monitoring system is provided which is ergonomic in design. Such a system allows coaches, trainers, and athletes to monitor various loads experienced by athletes in training, practice, and games.

The subject invention results from the realization, in part, that, in one example, a better physiological monitoring system includes a performance module, implemented in software, that calculates various loads experienced by an athlete (e.g., metabolic load, speed load, and biomechanical load) where each load is a function of a sensed parameter, various zones, and a weighting factor for each zone in order to arrive at a total load score which can be compared with a target load score so a coach or trainer can tailor practices and even change a practice schedule during a given practice in order to reach a desired target load for each athlete and/or for the team as a whole.

The subject invention features a load score system comprising a metabolic sensor for a subject configured to output metabolic data for the subject, a biomechanical load sensing subsystem for the subject configured to output biomechanical data, and a speed sensor subsystem for the subject configured to output speed data. One or more databases include zones and a weighting factor for each zone for metabolic data, biomechanical load data, and speed data. A performance module is responsive to the metabolic data, the biomechanical load data, and the speed data and the one or more databases and is configured to calculate a metabolic load score for the subject, calculate a biomechanical load score for the subject, and calculate a speed load score for the subject. An output module is configured to display the subject's calculated metabolic, biomechanical, and speed load scores.

In one version, the biomechanical load sensing subsystem and the speed sensor subsystem include an accelerometer such as a three axis accelerometer. The biomechanical load sensing subsystem includes means for processing the outputs of the three axis accelerometer and the speed sensor subsystem includes means for processing one output of the three axis accelerometer.

In one example, the performance module is configured to detect peaks in the biomechanical load data above a threshold, detect events based on the peaks, and for each event determine a zone for an a weighting factor to be applied to biomechanical load data to output a biomechanical load score for the subject. The speed sensor subsystem may be configured to identify steps and their frequency to determine speed data. The performance module is typically configured to determine a zone for and a weighting factor to be applied to the speed data to output a speed load score for the subject. The performance module is typically configured to determine a zone for and a weighting factor to be applied to the metabolic data to output a metabolic load score for the subject. In one preferred example, the metabolic sensor is a heart rate sensor.

Also, the performance module may include a clustering function configure to increase a load score by a predetermined factor if a predetermined number of load events occur within a predetermined time period.

The system may further include a garment and a band integrated with the garment including respiration sensing conductors and one or more additional conductors connected to a heard rate sensor. A dock is attached to the garment and the dock includes a receptacle with a cover secured to the band. A printed circuit board is associated with the cover and includes an accelerometer for the biomechanical load sensing subsystem and the speed sensor subsystem. A first connector component is electrically connected to the respiration sensing conductors and the at least one additional conductor. A housing is attached to the garment and receives the receptacle therein. A portable transmitting unit is removeably received in the dock and includes a second connector component mateable with the first connector component. In this way, the load scores can be transmitted to a base unit.

The subject invention also features a physiological monitoring method comprising determining heart rate data of a person, the person's speed data, and a biomechanical load data experienced by the person. A set of zones is established for metabolic load, speed load, and biomechanical load. Each zone has an upper threshold, a lower threshold, and a weighting factor. Based on the determined heart rate data, the time spent in each metabolic load zone is determined which is then multiplied by the weighting factor for each load zone and by the time spent in each zone to determine a metabolic load score. Based on the speed data, the determined speed data is allocated amongst the various speed zones based on the thresholds for each zone and the weighting factor for each zone is applied to determine a speed load score. Based on the biomechanical load data, the determined biomechanical load data is allocated amongst the various biomechanical load zones based on the threshold for each zone and the weighting factor is applied for each zone to determine a biomechanical load score. A total load score is based on the metabolic load score, the speed load score, and the biomechanical load score.

One physiological monitoring system in accordance with the invention features a metabolic sensor configured to output metabolic data for a subject, a biomechanical load sensing subsystem for the subject configured to determine a biomechanical load event, and a speed sensor subsystem for the subject configured to determine a step event and to calculate speed data based on step events and the time between step events. One or more databases store zones and a weighting factor for each zone for metabolic data, biomechanical load, and speed data. A performance module is responsive to the metabolic data, biomechanical load, and speed data and the one or more databases and is configured to calculate a metabolic load score for the subject by determining, for metabolic data, a zone for the metabolic data and a weighting factor for the metabolic data and, based on the zone and weighting factor, to determine a metabolic load score. A speed load score for the subject is calculated by determining, for speed data, a zone for the speed data and a weighting factor for the speed data, and based on the zone and weighting factor, to determine the speed load score. A biomechanical load score for the subject is calculated by determining, for biomechanical load event, a zone for the biomechanical load event and a weighting factor for the biomechanical load event, and based on said zone and said weighting factor, to determine a biomechanical load score.

One load scoring system in accordance with the invention features a first sensor configured to output a first type of data for a subject and a second sensor configured to output a second type of data for the subject. One or more databases store zones and a weighting factor for each zone for the first and second types of data. A performance module is responsive to the first and second types of data, the zones, and the weighting factors and is configured to calculate a first load score for the first type of data, and calculate a second load score for the second type of data. An output module is configured to display a subject's first and second load scores.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 14 is a schematic front top view of one embodiment of a stretchable band integrated into the shirt shown in FIGS. 12 and 13;

FIG. 15A is a highly schematic depiction showing conductors in the stretchable band of FIG. 14 when the band is in its relaxed state;

FIG. 15B is a highly schematic view similar to FIG. 15A except that now the distance between the conductors in the band has changed because the band is in its expanded state;

DETAILED DESCRIPTION OF THE INVENTION

Figure 1:
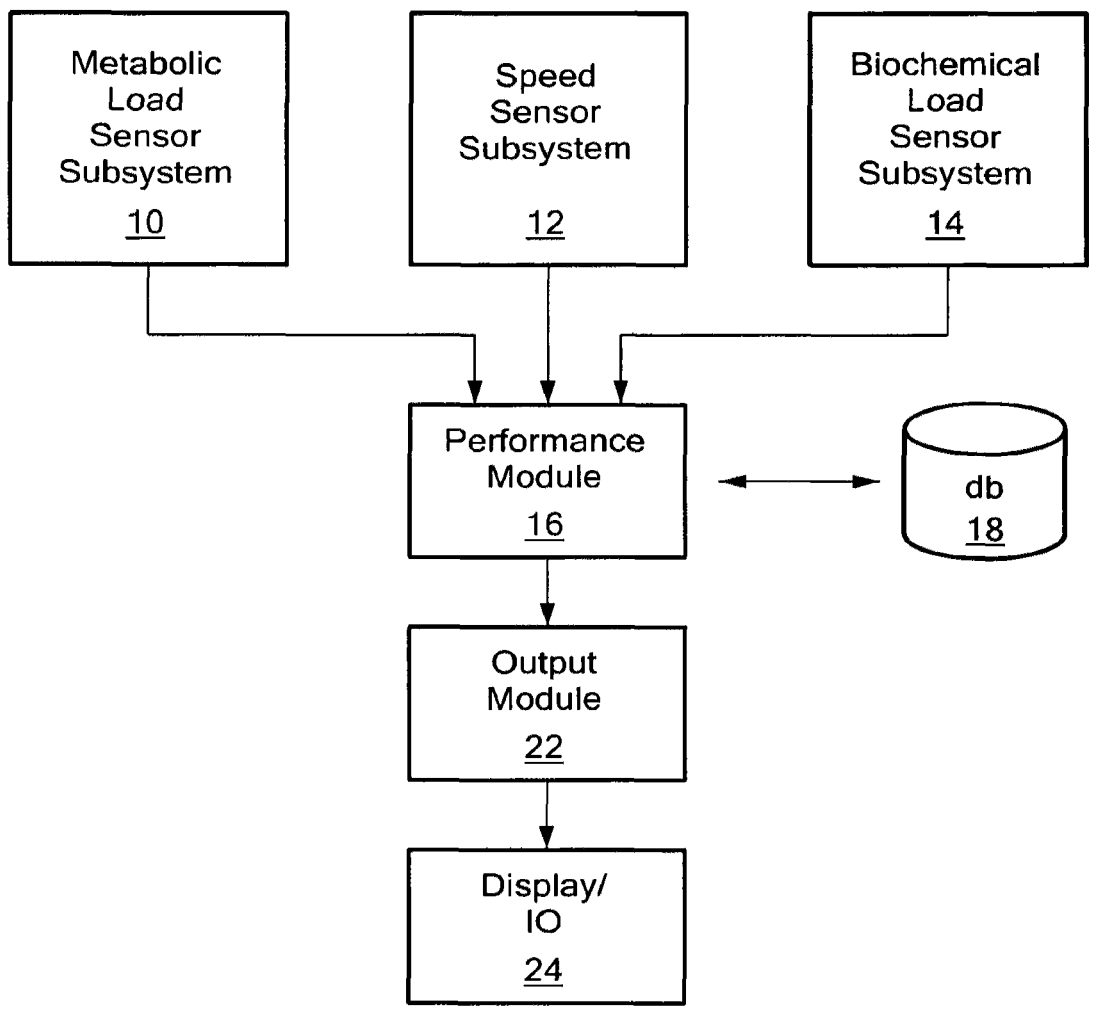
FIG. 1 is a highly schematic block diagram showing the primary components associated with an example of a physiological monitoring system in accordance with the subject invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows an example of one preferred physiological monitoring system including metabolic load sensor subsystem 10 typically including a heart rate sensor and/or respiration rate sensor. Speed sensor subsystem 12 and biomechanical load sensor subsystem 14 may share the same accelerometer. In one embodiment, the sensors are worn by the athlete and the data from the sensors is transmitted wirelessly to a base station and/or personal computer which is programmed with software associated with metabolic load sensor subsystem 10, speed sensor subsystem 12, and biomechanical load sensor subsystem 14. Each such subsystem may also include signal processing software and/or hardware as necessary.

Performance module 16 may be embodied in software running on a base station and/or a personal computer. Performance module 16 interfaces with one or more databases 18 populated with zone data, weighting factors, and, typically, calibration and other data. For example, athlete's names, ages, maximum heart rates, fastest speeds, maximum jump heights, and the like may be stored in database 18. Alternatively, performance module 16 and database 18 may be embodied in software operating on a controller or processor which is a component of the physiological sensor system worn or carried by the athlete. Or, certain calculations performed by performance module 16 may be carried out on the worn subsystem while other calculations are performed on the base station.

Output module 22 configures the athlete's metabolic, speed, and biomechanical load scores for display/IO section 24. Various views of the data can be selected via input module 20. Typically, display/IO and output module 22 are associated with a base station monitored by a coach.

Figure 2:
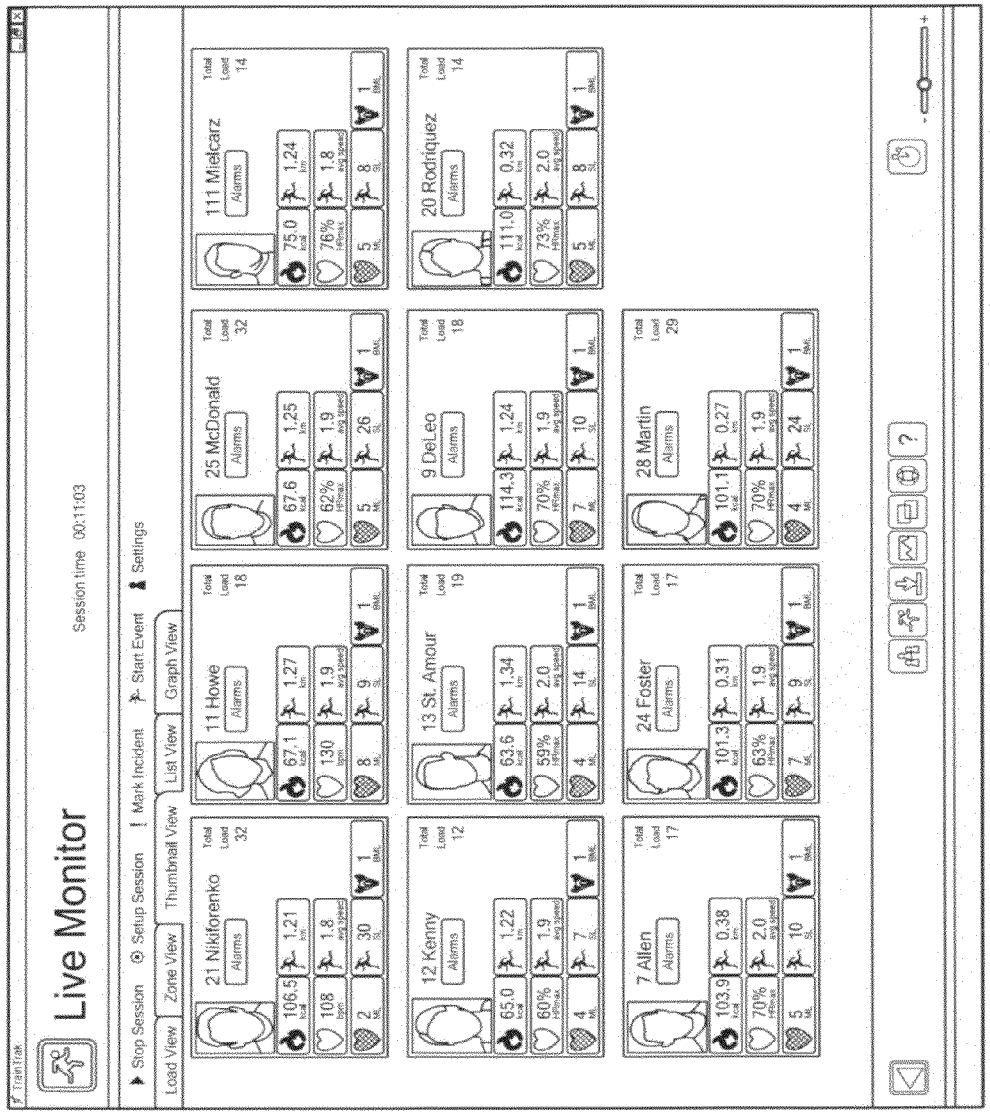
FIG. 2 is a depiction of the display shown in FIG. 1 displaying various data for several athletes during a practice in accordance with an example of the subject invention.
Figure 3:
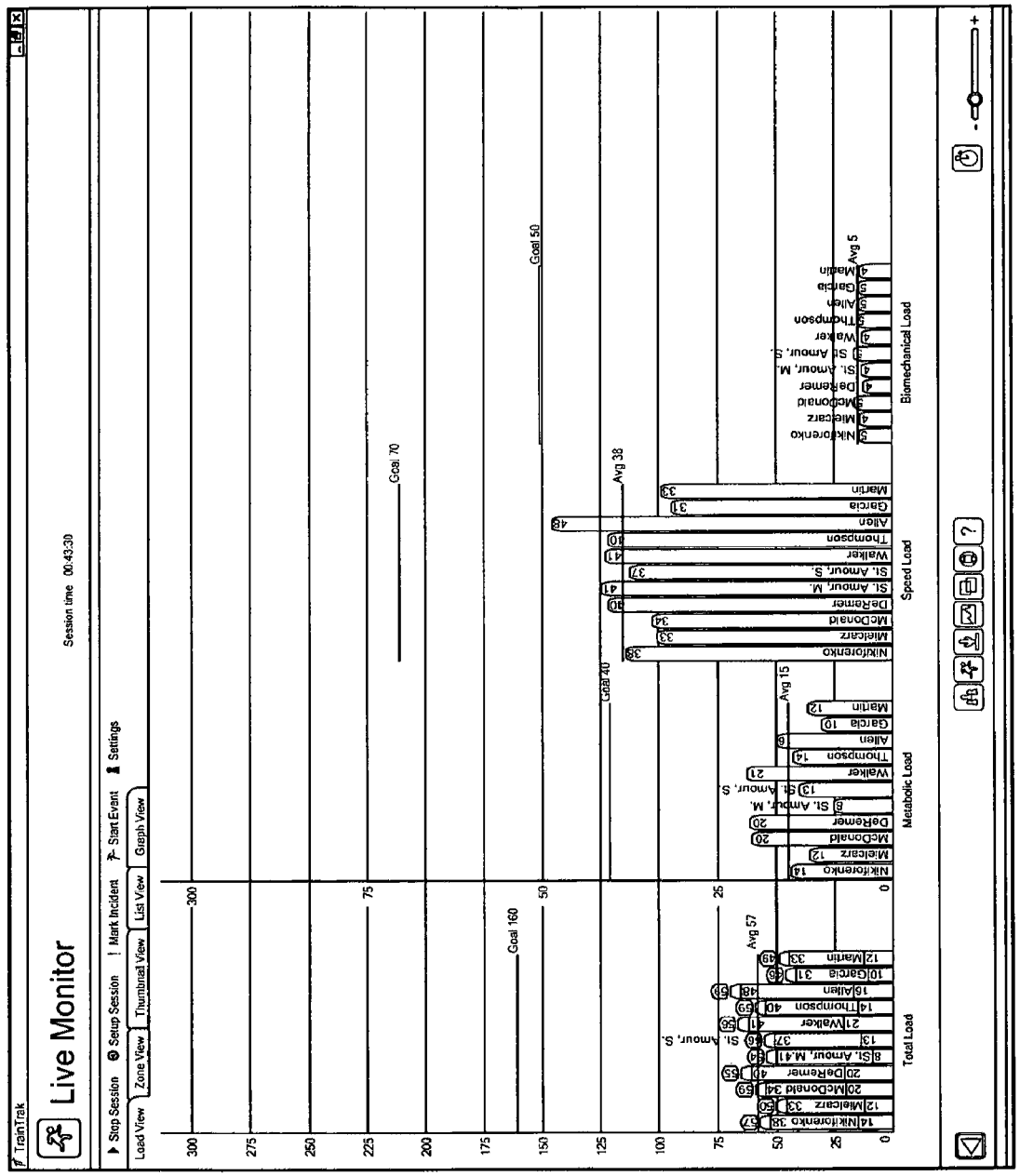
FIG. 3 is a depiction of the display shown in FIG. 1 showing various loads scores for the athletes.

FIG. 2 shows an example of a report generated on display 24, FIG. 1, wherein data for each athlete is displayed including the player's name, heart rate, average speed, metabolic load score (ML), speed load score (SL), and biomechanical load score (BML) as well as the athlete's total load score at any given time in the practice session. FIG. 3 shows each athlete's total load score, metabolic load score, speed load score, and biomechanical load score graphically displayed in relation to the other athletes' scores, an average, and a goal as set by the coach or trainer.

Typically, the metabolic zones include five individual zones each having a weighting factor as follows:

TABLE 1

METABOLIC LOAD
% MaxHR

| Zone | Lower Threshold | Upper Threshold | Weighting Factor |
|---|---|---|---|
| 5 | 95% | 100% | 1.75 |
| 4 | 85% | 95% | 1.4 |
| 3 | 75% | 85% | .875 |
| 2 | 65% | 75% | .4375 |
| 1 | 50% | 65% | .175 |

These zone, thresholds, and weighting factors are stored in database 18, FIG. 1.

Similarly, the speed and biomechanical zones may be established in database 18 as follows:

TABLE 2

SPEED LOAD
m/sec

| Zone | Lower Threshold | Upper Threshold | Weighting Factor |
|---|---|---|---|
| 5 | 8 | — | 8 |
| 4 | 6 | 8 | 5 |
| 3 | 5 | 6 | 2 |
| 2 | 3 | 5 | 1 |
| 1 | 1 | 3 | 0 |

TABLE 3

BIOMECHANICAL LOAD
Gs

| Zone | Lower Threshold | Upper Threshold | Weighting Factor |
|---|---|---|---|
| 5 | 8 | — | 9 |
| 4 | 5 | 8 | 6 |
| 3 | 3 | 5 | 3 |

TABLE 3-continued

BIOMECHANICAL LOAD
Gs

| Zone | Lower Threshold | Upper Threshold | Weighting Factor |
|---|---|---|---|
| 2 | 2 | 3 | 2 |
| 1 | 1 | 2 | 1 |

The zones and weighing factors will vary depending on a number of factors including the type of sport, the coach's settings, and the like.

Performance module 16 is configured to determine, based on the data output of metabolic load sensor subsystem 10, the time spent in each metabolic load zone of Table 1 and multiply the weighting factor for each zone by the time spent in each zone to determine a metabolic load score. Referring to Table 2, performance module 16 allocates the determined speed data amongst the various speed zones of Table 2 based on the thresholds for each zone and applies a weighting factor for each zone to determine a speed load score. An event based technique may also be used.

Performance module 16 also allocates the determined biomechanical load data against the various biomechanical load zones of Table 3 based on the thresholds for each zone and applies the weighting factor of Table 3 for each zone to determine a biomechanical load score. A running total of each load score is calculated and displayed. A total load score is also calculated based on the metabolic load score, the speed load score, and the biomechanical load score. In one example, the total load score is a summation of all the individual load scores. In other examples, the individual load scores can be weighted before calculating the total score.

In one example, suppose athlete A's heart rate monitor (10, FIG. 1) outputs data indicating athlete A, during a given practice, spends five minutes in zone five, five minutes in zone four, five minutes in zone three, twenty-five minutes in zone two, and thirty-minutes in zone one. Applying the weighting factors for each of these zones, athlete A's metabolic load for that practice, as determined by performance module 16, is 37.1875 calculated thus:

| ZONE | TIME | WEIGHT | SCORE |
|---|---|---|---|
| 5 | 5 minutes | 1.75 | 8.75 |
| 4 | 5 minutes | 1.4 | 7.00 |
| 3 | 5 minutes | .875 | 4.375 |
| 2 | 25 minutes | .4375 | 10.9375 |
| 1 | 35 minutes | .175 | 6.125 |
|  |  |  | 37.1875 |

Figure 4:
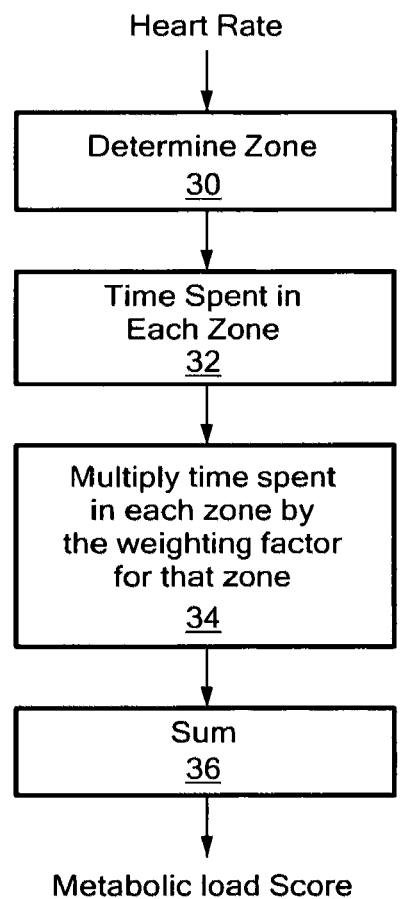
FIG. 4 is a flow chart depicting how the performance module shown in FIG. 1 determines a metabolic load score for a subject in accordance with an example of the invention.

FIG. 4 depicts how performance module 16, FIG. 1 determines the metabolic load score of a person. Based on heart rate data from metabolic load sensor subsystem 10, FIG. 1, the zone is determined, step 30. For example, a heart rate which is 87% of a person's maximum heart rate is determined to be zone 4 based on the data stored in database 18, FIG. 1. The person's stored maximum heart rate can be a fixed number, a heart rate based on age, or a heart rate based on the person's actual heart rate either entered manually via input module 20 or detected automatically via metabolic load sensor subsystem 10 when the person is required to perform some task which will raise his heart rate in a prescribed way in order to calculate the maximum heart rate.

In step 32, FIG. 2, the time in each zone is calculated and in step 34, the time spent in each zone is multiplied by the weighting factor of each zone. Summing these calculations, step 36, results in a metabolic load score. Performance module 16 adds this score to the speed load score and the biomechanical load score to determine a total load score.

Output module 22, FIG. 1 stores and/or displays all the load scores on display 24, for example, a base station wirelessly receiving data from the sensors worn by the person and/or a personal computer or handheld device linked to the base station. The software discussed herein may reside on a base station, PDA, or personal computer and/or may be split amongst the various platforms.

The software also typically allows for set ups of team and player data, live monitoring of physiological data for each player, the ability to download and database data, and the ability to provide an analysis, reports, and assistance. A team set up screen allows the coach or trainer to name the sport adjusted time, weighting of load scores based on the sport or activity being monitored, and adjust the positions played by each athlete, and player status. In a team member screen, rosters can be imported, pictures can be associated with each team player, and each player's number, name, date of birth, weight, height, maximum heart rate, resting heart rate, academic year or year on the team, maximum speed, and the like can be entered and edited. Alarms can be included and can be activated based on a player by player basis. All of the alarms can be set to sound an alert if a maximum or a minimum quantity is reached. Settable alarms can include providing an output if one or more goals are not reached or are projected to be exceeded by a predetermined amount, alarms for each load score, and the like. Zone alarms and cumulative alarms are also possible. A planning module allows coaches to plan practices and drills and the ability to add a session name, and then define events in the sessions each with variables in the fields of cumulative targets, conditions, cumulative alarms, zone alarms, and positions. A calibration module allows coaches to measure maximum heart rate, resting heart rate, and respiration volume. Step frequency at walking, running, and sprinting speeds can also be measured and calculated. For biomechanical load, the calibration module allows the coach to measure a maximum force achieved during a vertical jump and during an acceleration/de-acceleration event.

A live monitor screen output allows a coach to start a session, set up a session, mark an incident, start an event, and the like. Goals for the players can be set including goals for metabolic load, speed load, biomechanical load, total load, time, distance, calories, and the like. Numerous different outputs are possible in accordance with the subject invention including a load view where the coach is able to view the load score for each player in the categories of total load, metabolic load, speed load, and biomechanical load. In a zone view, the current performance of all players in percentage of maximum heart rate, maximum speed, calories per minute, respiration rate, and the like can be viewed. A coach is able to view each of the players statistics for time above the target, heart rate, time above the target respiration rate, time above the target speed, total distance, total calories, number of sprints, the time in a sprint zone, the time in a run zone, metabolic load, speed load, biomechanical load, total load, and number of biomechanical events. Team averages for each parameter, position averages, and the like can also be displayed. In a graph mode, a selectable number of players, positions, or the entire teams can be viewed via graphs relating to heart rate, speed, calories per minute, respiration rate, metabolic load, speed load, biomechanical load, and total load. In the analysis mode, results can be reviewed and compared with previous results, players can be compared with each other, players workouts can be compared with each other, and various graphs over time can be established showing a plot of the total load, metabolic load, speed load, and/or biomechanical load viewed by intervals such as monthly, every three-months, every six-months, or a custom length of time. An analysis can also be performed for single events, or trends over time. The analysis can be linked to a reporting function for storing reports saved in the analysis segment of the software.

The result is a highly versatile system enabling a coach or trainer to change a practice as necessary and compare real time player performance versus goals established, view one players performance in view of the rest of the team's performance, and to analyze a player in one position on the team with other players in that same position.

The system can also be used to monitor an athlete rehabilitating after an injury. The player's loads at each practice or training session can be controlled per a prescribed schedule, and comparisons can be made to the athlete's pre-injury status thus indicating whether he is ready return to play.

Event based clustering awards are also possible. For example, suppose that three significant biomechanical load events happen in a very short time frame. In such case, performance module 16, FIG. 1 can detect such a cluster and increase the overall score by some predetermined factor such as 50%. For collisions, as determined by performance module 16 based on the output of biomechanical load sensor subsystem 14, performance module 16 may detect a collision (for example, any accelerometer output greater than 10 gs) and provide an identification of a collision event and also enable an increased score factor.

Figure 5:
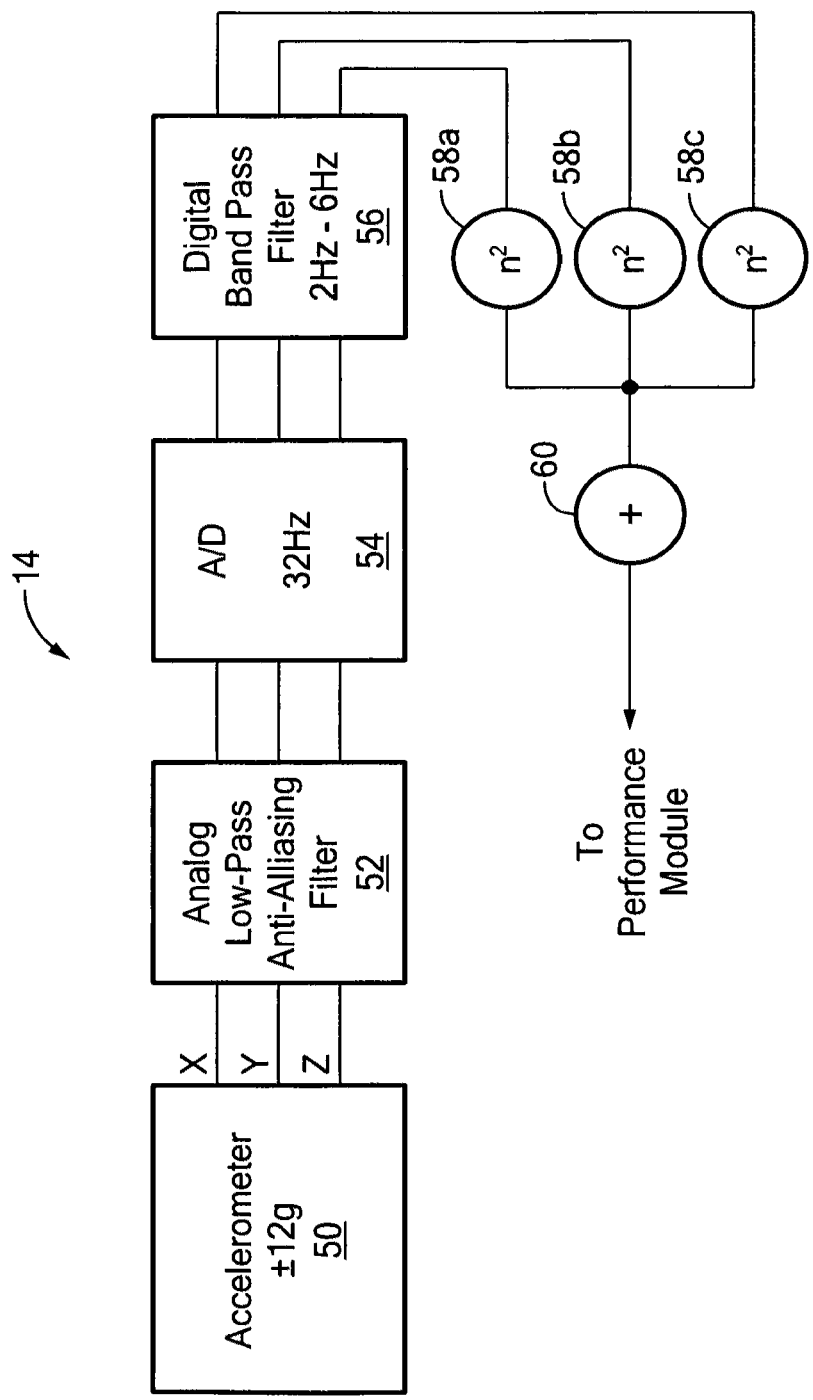
FIG. 5 is a block diagram showing the primary components associated with an example of the biomechanical load sensor subsystem shown in FIG. 1.

FIG. 5 shows an example of a biomechanical load sensor subsystem 14 including three axis accelerometer 50. The outputs of accelerometer 50 are passed through analog low-pass anti-aliasing filter 52 and converted to digital signals at 32 Hz A/D converter 54. These digital signals are filtered via digital band pass filter 56 (2 Hz-6 Hz) and each filtered signal is squared as shown as 58a-58c and added together as shown at 60. This signal is then input to performance module 16, FIG. 1.

Figure 6:
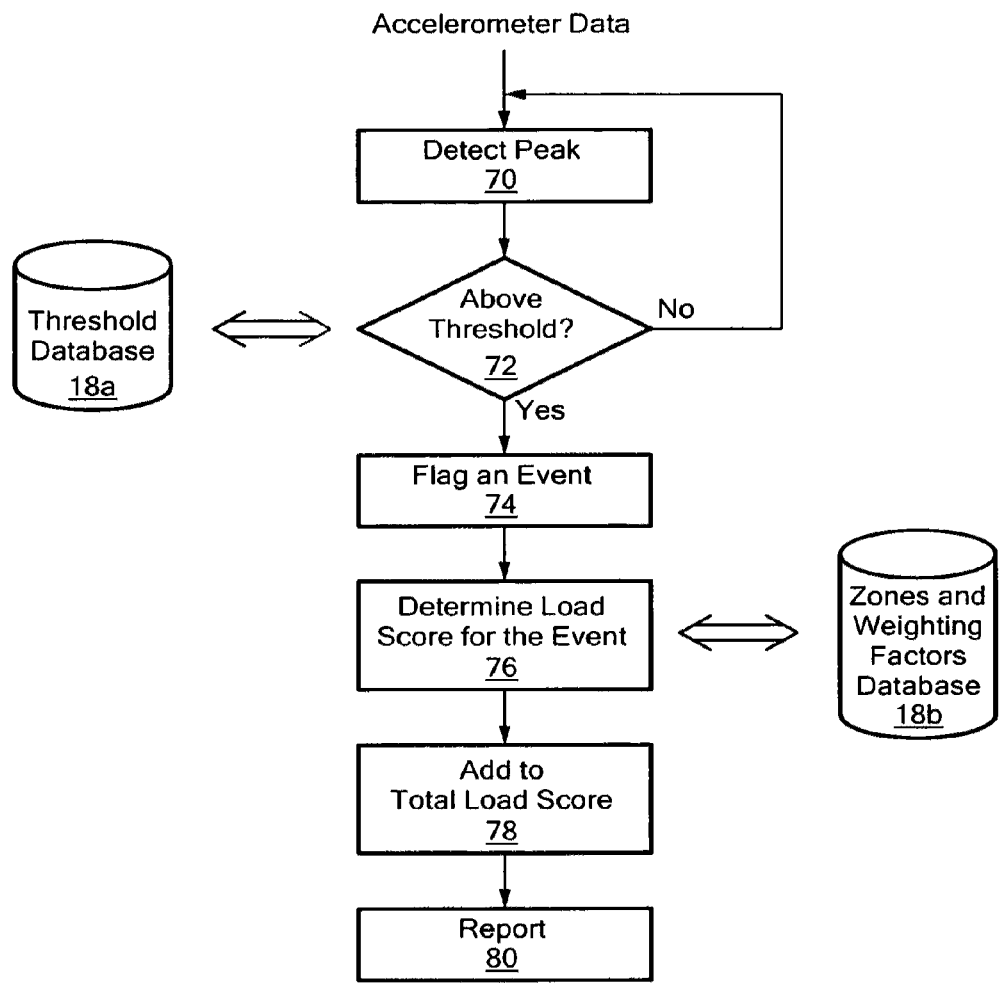
FIG. 6 is a flow chart depicting the primary steps carried out by the performance module shown in FIG. 1 to determine a subject's biomechanical load score in accordance with an example of the invention.

Software, (typically operating on a microcontroller or equivalent) then detects any peaks, step 70, FIG. 6. If the peak is above the thresholds stored in database 18a, as shown at step 72, then a biochemical load event is flagged, step 74, when the signal crosses the threshold on the down slope. The load score for that event is then determined, step 76, based on the zones and weighting factors for each zone (see Table 3 above) using the data stored in database 18b. The load score for each event is then added to the current total biomechanical load score, step 78, which is reported, step 80 (e.g., via output module 22, FIG. 1 for display on display 24 as shown in FIG. 3).

Figure 7:
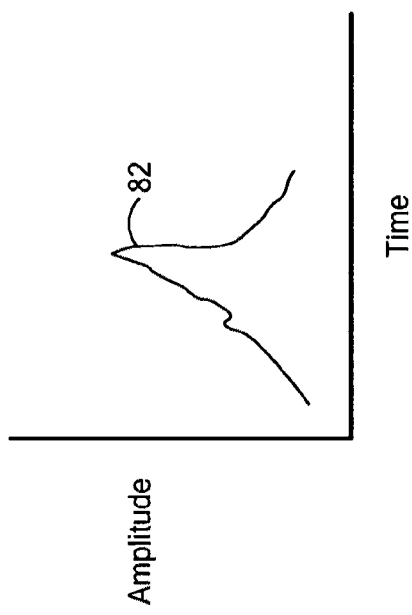
FIG. 7 is a graph showing how peaks are detected in order to flag events in accordance with the processing depicted in FIG. 6.

For example, suppose an athlete has a present biomechanical load score of 10 and then he jumps resulting in signal output at 60, FIG. 5 which looks like that shown in FIG. 7. Peak 82 is detected and it is above the threshold stored in database 18a. Peak 82 is flagged as an event. The amplitude of peak 82 is in zone 3 of Table 3. Applying the weighting factor (step 76, FIG. 6) results in a biomechanical load score of 3 for this event and now the athlete's total biomechanical load score is 13.

Figure 8:
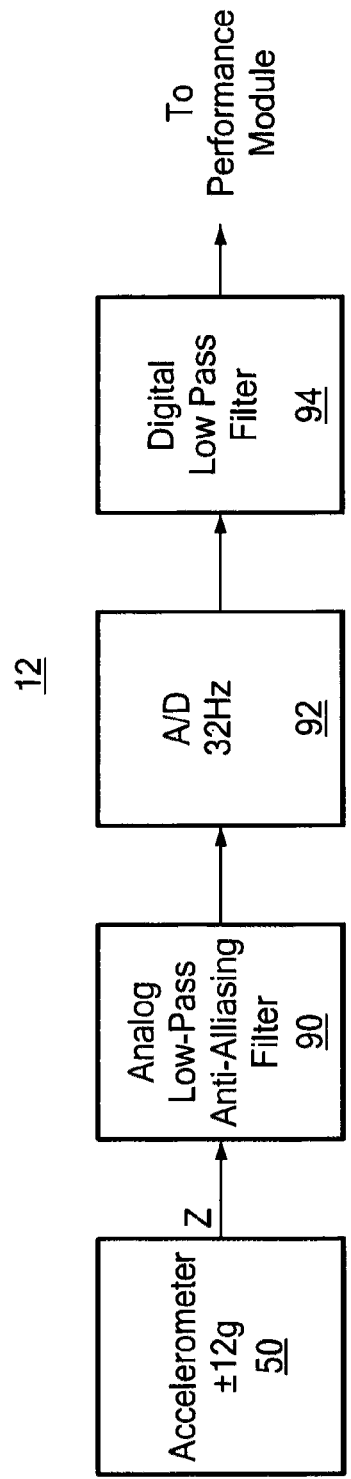
FIG. 8 is a block diagram showing the primary components associated with an example of a speed sensor subsystem shown in FIG. 1.

In one example, speed sensor subsystem 12, FIG. 8 uses the Z axis output of accelerometer 50 which is passed through analog low-pass anti-aliasing filter 90 and 32 Hz A-D converter 92. After filtering this digital signal in digital low pass filter 94, the output is used to identify steps, step 100, FIG. 9. A rules engine 102 can be used to identify steps as shown.

Figure 10C:
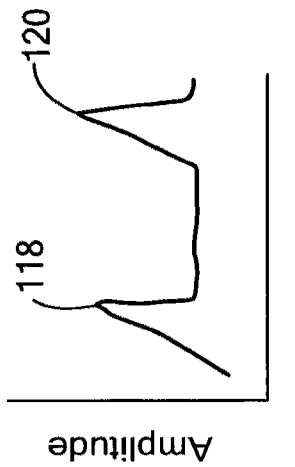
FIGS. 10A-C are graphs depicting how steps are identified during the processing depicted in FIG. 9.
Figure 10B:
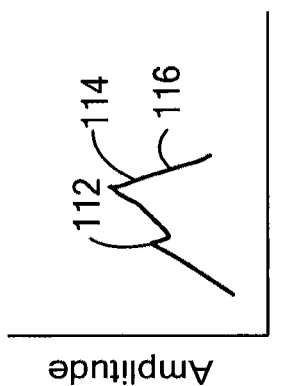
Figure 10A:
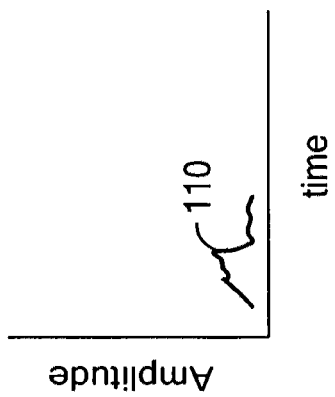

For example, a peak 110, FIG. 10A, which is below a threshold (e.g., 1 G) is not considered to be a step event. A peak above the threshold as shown at 112 (FIG. 10B) followed by a higher peak 114 followed by a drop off 116 greater than or equal to one-half of peak 114 is characterized as a step (i.e., peak 112 is likely a heel strike and peak 114 is likely a toe strike). Another possible rule is that peaks 118 and 120, separated by too long a time as shown in FIG. 10C, do not constitute a step.

Figure 9:
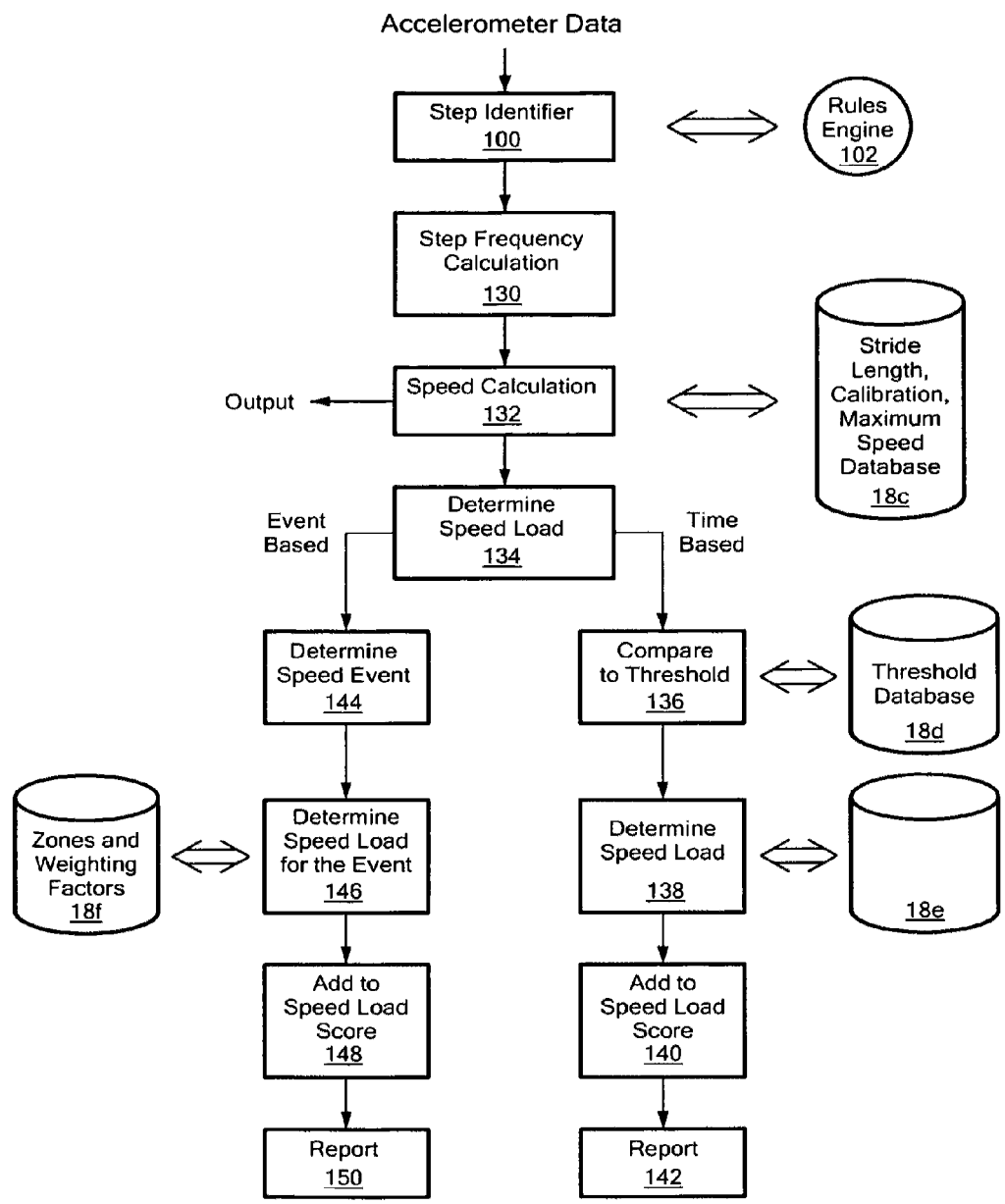
FIG. 9 is a flow chart depicting, in one example, the primary steps associated with a speed sensor subsystem and/or the performance module shown in FIG. 1 for determining a subject's speed load score.

Step frequency calculator 130, FIG. 9 then determines the time between steps and speed calculator 132 determines speed. This data may be output for each athlete as shown in FIG. 2 and the athletes speed may also be averaged as shown. Distance may also be calculated based on the elapsed time. Speed calculator 132 may use data stored in data base 18c (e.g., stride length for that athlete, an average stride length, a maximum speed for the athlete, calibration data, and the like) since speed is a function of step frequency and one or more parameters such as stride length. Typically, steps 100, 130 and 132 are performed in software implemented in speed sensor subsystem 12, FIG. 1.

Once an athlete's speed has been determined, performance module 16 calculates the speed load. Again, software is typically used. The speed load, step 134, FIG. 9, is then determined using an event based routine and/or a time based routine. For time based criteria, a given speed counts toward a load score when it is above a minimum preset threshold, step 136, stored in database 18d. The speed load is determined, step 138, for example, using Table 2 above (stored in database 18e). The speed load is then added to the present load score, step 140, and reported, step 142.

For event based speed load determinations, a speed event is determined, step 144, based on the speed over a given stored time interval. For that speed event, the speed load is determined, step 146, using the zones and weighting factors (see Table 2) stored in database 18f. The present speed load score is added to the athlete's total speed load score, step 148, and reported, step 150. Reported speed load scores for each athlete are shown in FIG. 2-3.

For example, suppose an athlete has a current speed load score of 30. Speed load calculator 132, FIG. 9 determines the athlete is running at nine meters per second and at step 144 this event last for ten seconds. So, a speed event is detected. At step 146, the athlete's speed load score for that event is determined to be 8 applying the weighting factor of Table 2 for a speed event in zone 5. The athletes speed load score is now 38.

For speed load calculations based on time in zone, assume a subject spends the following time in each zone:

| ZONE | TIME | WEIGHT/MINUTES | SCORE |
| --- | --- | --- | --- |
| 5 | 0:45 | 8 | 6 |
| 4 | 2:15 | 5 | 11.25 |
| 3 | 8:45 | 2 | 17.5 |
| 2 | 16:15 | 1 | 16.25 |
| 1 | 27:30 | 0 | 0 |
| | | | 68.5 |

The time in minutes is multiplied by the score weight for that zone. Then the total for each zone is summed for speed load score.

Another possible feature includes clustering, wherein, for example, an athlete's load score is increased by some factor (e.g., 50%) for events which occur within a short pre-determined period of time. For example, if an athlete experiences three biomechanical load events in zone three all within six seconds, then the calculated biomechanical load score can be automatically increased by 50%.

Figure 11:
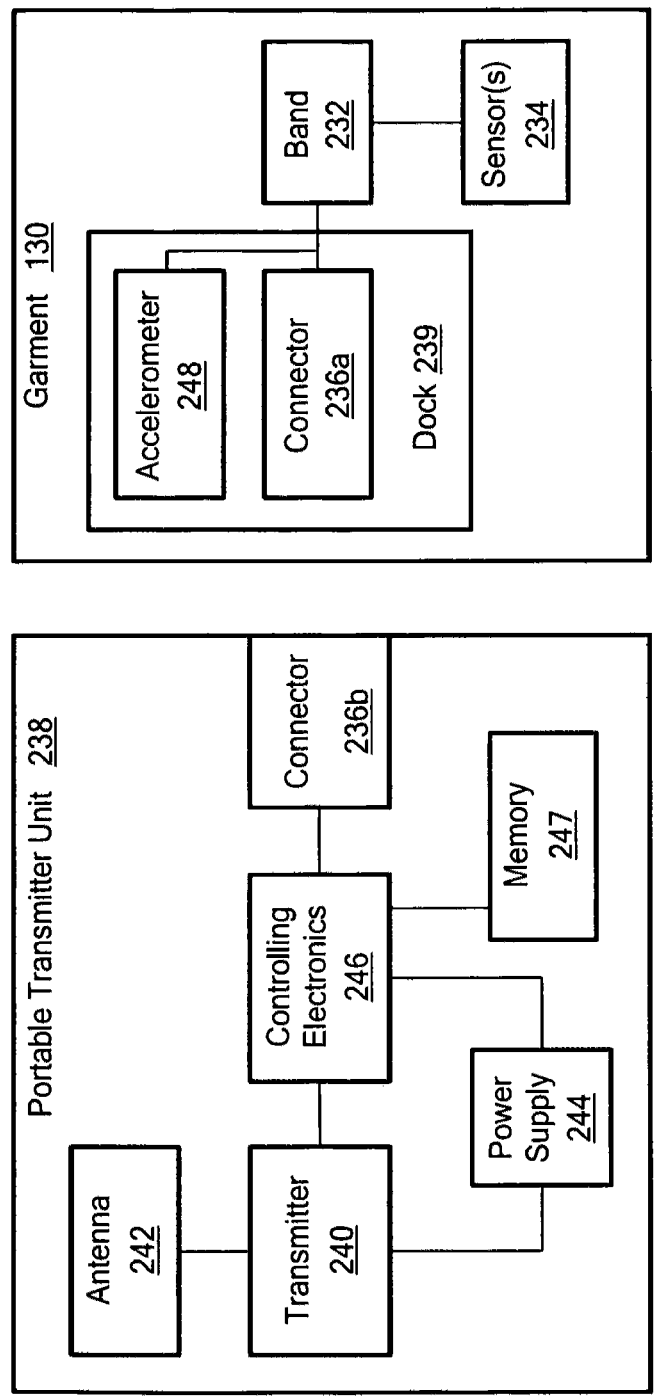
FIG. 11 is a block diagram depicting the primary components associated with an example of a physiological monitoring system in accordance with the subject invention.

A new physiological monitoring system in accordance with the subject invention may include, in one example, a garment (e.g., a shirt) 230, FIG. 11 including a band 232 associated therewith. The band may include sensing means and/or may be attached and/or electrically connected to one or more sensors 234. See U.S. patent application Ser. No. 11/807,449 incorporated herein by this reference. The band includes conductors which are connected to connector 236a of dock 239. Dock 239 typically includes accelerometer 248. Accelerometer 248 is included to provide data indicative of the users speed and/or the load experienced by the user. Connector 236a may include conductive pads, for example.

Portable transmitting unit 238, removeably received in dock 239, includes connector 236b which mates with connector 236a of dock 239 to receive the signals transmitted by the conductors in band 232 and the signals from accelerometer 248. Connector 236b may include pogo pins, for example, which mate with the conductive pads of connector 236a when portable transmitting unit 238 is located in dock 239. Portable transmitting unit 238 is configured to wirelessly transmit signals via transmitter 240 and antenna 242 to a base unit or the like. Performance data can be stored in memory 247 for later transmission. Portable transmitting unit 238 is typically small, has a low profile, and is removed from the garment so that the garment can be washed. Portable transmitting unit 238 also typically includes power supply 244 providing power to transmitter 240 and controlling electronics 246 which receives and processes signals from connector 236b and controls transmitter 240 accordingly. Other signal processing components such as A/D converters, signal processing circuitry, and the like are not shown in FIG. 11. Controlling electronics 246 may include the subsystems shown in FIG. 1, for example metabolic load sensor subsystem 10, speed sensor subsystem 12, biomechanical load sensor subsystem 14, performance module 16, and the like.

Figure 12:
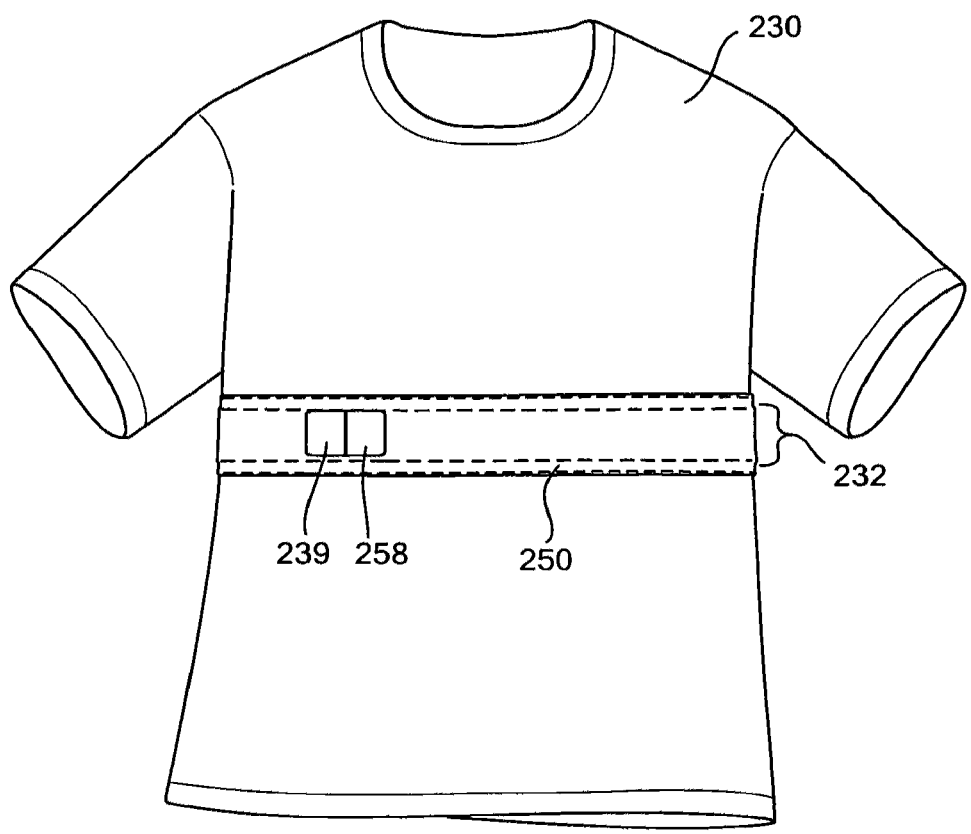
FIG. 12 is a schematic front view of an example of a physiological monitoring shirt in accordance with the subject invention.

An easily washable shirt 230, FIG. 12 can be made of any fabric (e.g., cotton) but typically is made of a "compression" fabric often including Lycra material (e.g., the POLARTEC® material available from Malden Mills). For additional comfort, moisture management and the like, shirt 230 may include fabric fibers of variable loft, thickness or density placed to coincide with preferred body locations where desired. Sewn or bonded to the inside (or outside) of this or any conventional shirt is a stretchable circumferential band the outline of which is shown in FIG. 12 at 232. The result in one version is a shirt free of any atypical seams or the like. The band includes an integrated respiration detection subsystem, sensors, signal transmission conductors for the sensors, and a connection subsystem. Cover 250, if used, also typically made of compression or plush material, may be sewn and/or bonded over the band. The band 232 may include an integrated respiration detection subsystem, one or more sensors, and signal transmission conductors for the sensors. Portable transmitting unit 238 is received in dock 239 attached to shirt 230. This electronics module wirelessly transmits respiration and other (e.g., ECG) physiological status signals to a remote unit where the wearer's ECG, respiration rate, skin temperature, heart rate, speed, and activity level or load may be displayed and/or recorded.

Figure 13:
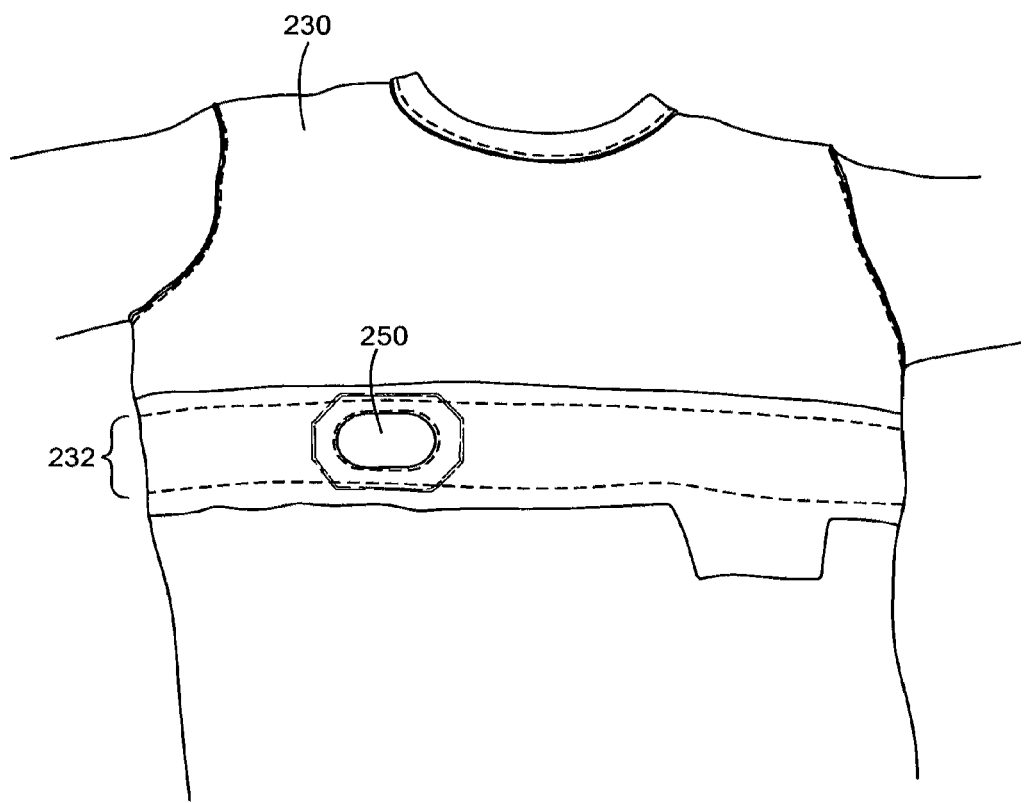
FIG. 13 is a schematic front view of the inside of the shirt shown in FIG. 12.

FIG. 13 shows the inside of shirt 230 and again the outline of the circumferential band can be seen at 232. FIG. 13 also shows one exposed ECG electrode 250a inside the shirt for monitoring the wearer's heart rate. Additional exposed ECG electrodes may be attached to band 232. See U.S. patent application Ser. No. 11/807,449. Other sensors may be added and may be integrated with the band or connected to it. Examples include thoracic bioimpedance sensors or biomechanical sensors, one or more temperature sensors connected to the signal transmission elements of the band.

Note the lack of any loose wires inside or outside the shirt. Other than the electrodes, and/or any sensors or an optional cover, only shirt material touches the wearer's skin. Except for electronics module 238, FIG. 12 and the slight outline of the band, shirt 230 looks just like a normal shirt. Shirt 234 is thus comfortable, aesthetically pleasing, quickly donnable and doffable, and easy to use. It can be worn under other clothing, it is easily cleaned, it can wick away body perspiration, and it does not interfere with the activities of or duties carried out by the wearer. Physiological parameters measured are more accurate because the portion of the shirt including the stretchable band can hold sensors in more intimate contact with the wearer's body. Also, the sensors are located away from the module so as the module moves with the movement of the wearer the sensors are not impacted, resulting in less motion artifact and further increased accuracy of measurements.

Stretchable band 232 is shown alone in FIG. 14. Integrated with the fabric of band 232 are conductors (typically insulated wires) in a flexible configuration typically in-plane nested pairs as shown at 260a-260f. The nested pairs may be sinusoidal as shown, or any other suitable configuration such as triangle wave or zig-zag (not shown). One conductor pair 260a is shown more clearly in FIGS. 15A-15B and can be used as a component of a respiration sensing subsystem. When the band is relaxed because the wearer has exhaled, the distance between wires 270a and 270b is $d_1$, FIG. 15A. When the band is stretched because the wearer has inhaled, the distance between wires 270a and 270b is $d_2$, FIG. 15B. In this way, by configuring band 232, FIG. 14 to be circumferential about the wearer's chest and snug thereabout in the relaxed configuration, when the wearer breathes, any nested conductor pair in the band can be used as a respiration detector.

An electronics module includes a circuit which detects changes in, for example, capacitance as the adjacent nested circumferential conductors move away from and towards each other as stretchable band 232, FIG. 14 expands and contracts as shown in FIGS. 15A-15B. That change in impedance (e.g. capacitance) is thus indicative of respiration rate, indicating frequency of breaths taken by the wearer, as well as the depth or volume of each breath. In a plot of impedance and time, peak to peak distance is indicative of breathing rate or frequency.

Other conductor pairs can also be used for sensing respiration but typically at least a few conductors are reserved for signal transmission from sensors such as the ECG electrodes to an electronics module and possibly between the electronics module and these and other sensors or processing units which may be included on or electrically connected to the band.

Figure 16:
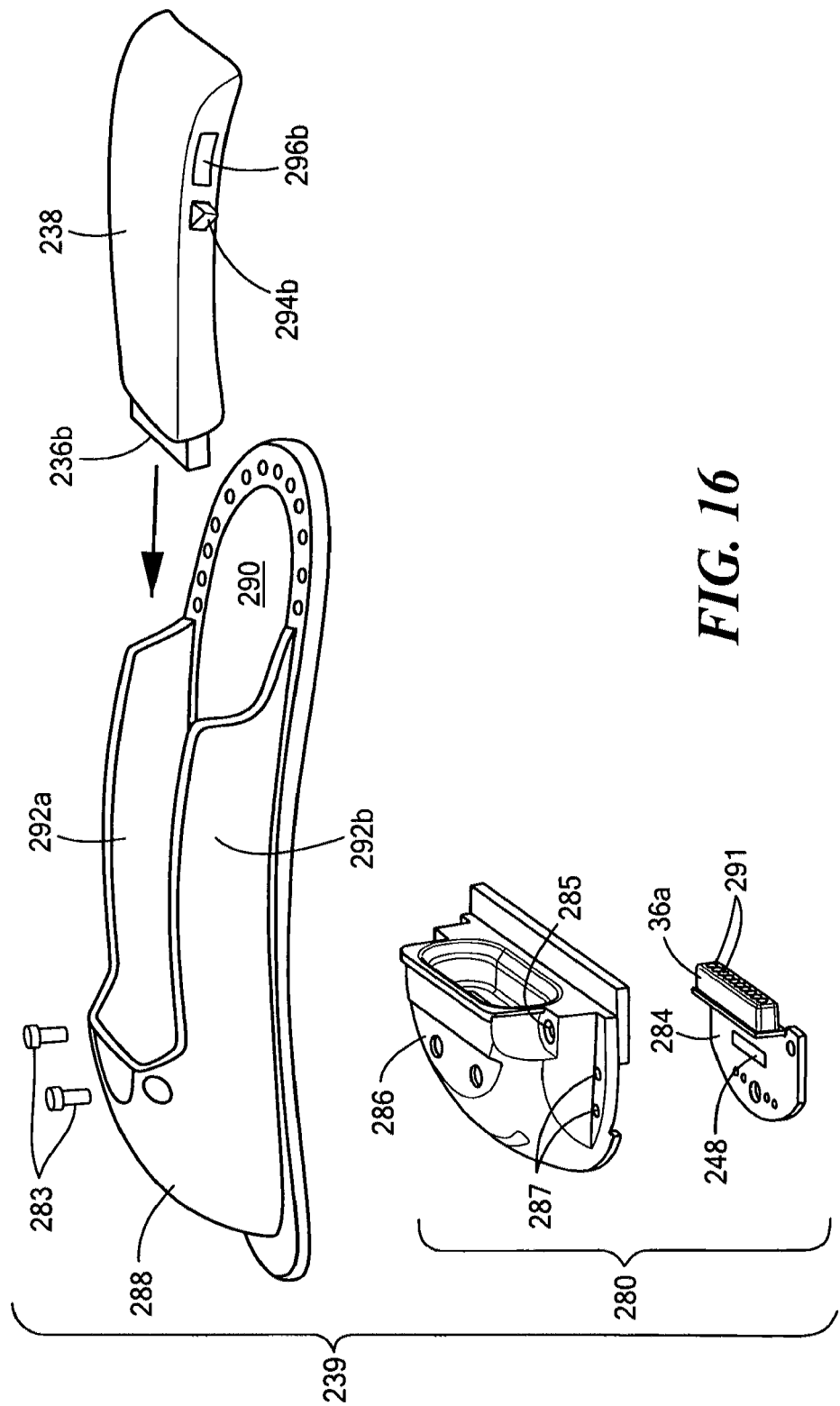
FIG. 16 is a schematic exploded front view showing the primary components associated with an example of a docking station attached to the shirt shown in FIGS. 12 and 13 for a portable transmitting unit shown.

FIG. 16 shows an example of dock 239 which is attached to shirt 230, FIG. 12. Dock 239 includes receptacle 280 which includes printed circuit board 284 encapsulated (potted) in cover 286. Cover 286 is secured (e.g., sewn and/or glued) to band 232, FIGS. 12-14. Holes 287 can be used to sew cover 286 to the band. Conductors in the band and/or conductors connected those conductors extend through board 284 where they may be sealed against water ingress and then routed to connector 236a. Connector 236a may include conductive pads 291 or female connectors, or the like. Board 284 may also includes accelerometer 248 (typically a three axis accelerometer) the output of which is routed via printed circuit board 284 to connector 236a. Associating accelerometer 248 with dock 239 instead of portable transmitting unit 238 has several advantages. Dock 239 moves in a way more closely related to the user's movements. Also, portable transmitting unit 238 can now be made smaller, and it is rendered less expensive and less complex.

Dock 239 can be attached at any location on the garment and stretchable bands are used to electrically connect dock 239 to sensors located elsewhere on the garment and/or to a respiration sensing band as disclosed above. Cover 286 may be sealed (e.g., ultrasonically welded) to board 284. Fasteners 283 secure cover 286 to housing 288 via bosses (e.g., boss 285) in cover 286.

Figure 17:
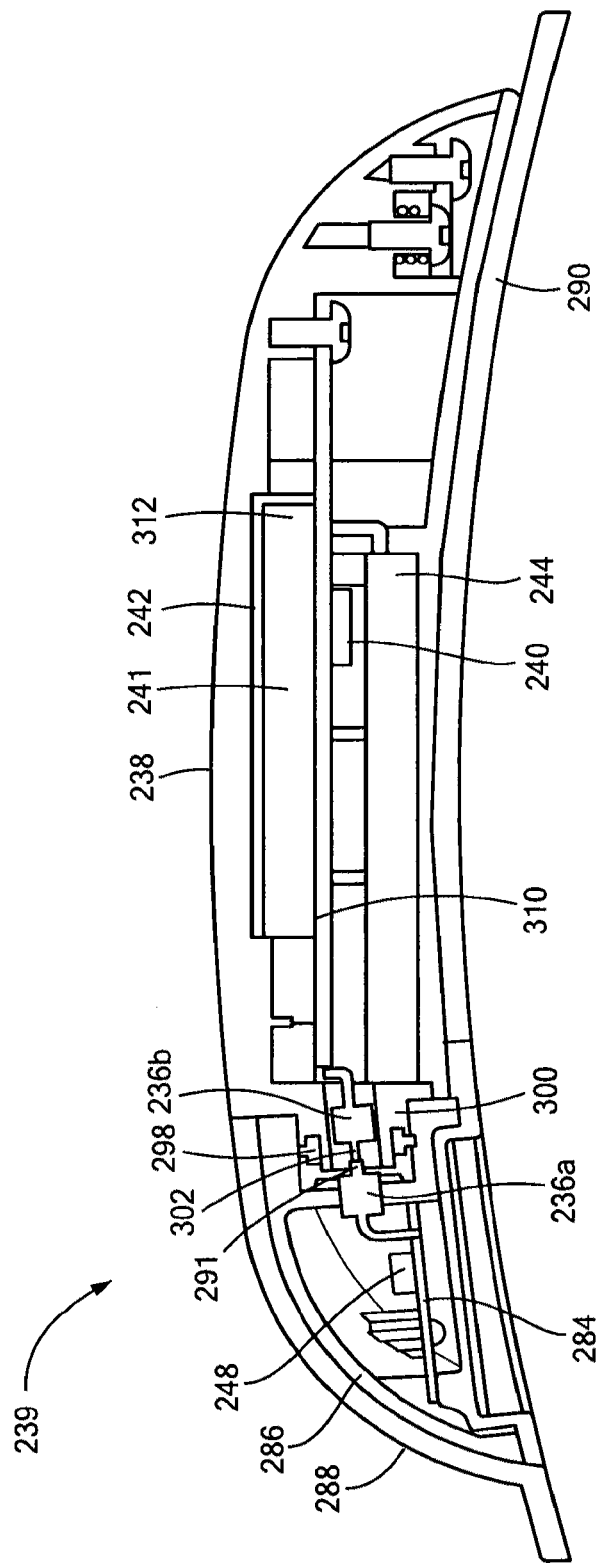
FIG. 17 is a schematic cross-sectional side view of a portable transmitting unit in accordance with the subject invention inserted into the docking station on the garment.

Housing 288 is attached (e.g., sewn and/or glued) to shirt 230, FIG. 12 and receives the portable transmitting unit 238, FIGS. 16-17 therein. Portable transmitting unit 238 includes connector 236b which mates with connector 236a of dock 239 when portable transmitting unit 238 is slid into dock 239. In this way, the portable transmitting unit receives respiration, heart rate, and accelerometer data from the shirt and records the data via memory 247, FIG. 11 and/or transmits it to a base station for the monitoring of a person wearing the shirt (e.g., by a coach, trainer, commander, or the like) via transmitter 240. The components shown in FIG. 16-17 may be made of plastic.

In this preferred example, housing 288 includes tongue member 290, FIGS. 16-17 and side rails 292a and 292b, FIG. 16 upstanding from tongue member 290 receiving portable transmitting unit 238, FIGS. 16-17 therebetween. Rails 292a and 292b, FIG. 16 curve inwardly over tongue member 290 to retain the portable transmitting unit in place forming a dovetail-like interlock between the portable transmitting unit and the dock. Portable transmitting unit 238, FIG. 18 also includes a latch mechanism engaging the portable transmitting unit in housing 288. The latching mechanism shown in FIG. 18 includes spaced spring loaded fingers 292a and 292b releasably received in indents 294a and 294b, respectively, in housing 288. Buttons 296a and 296b, when pushed, disengage fingers 292a and 292b from indents 294a and 294b to allow portable transmitting unit 238 to be removed from housing 288.

When portable transmitting unit 238 is in housing 288, the combination is typically no larger than 4 inches wide, 8 inches long, and 3 inches high. A prototype unit measured 4 inches long, 2 inches wide and 0.6 inches high. As shown in both FIGS. 16 and 17, housing 288 has a concave conforming shape and portable transmitting unit 238 is shaped to fit the shape of the housing. The result is a low profile, small, conforming unit which can be used by athletes, soldiers, or even animals. Padding may be added behind substrate 282 as well as over housing 288 for additional comfort and safety.

O-ring seal 298, FIG. 17 about connector 236b housing 300 of portable transmitting unit 238 helps insure a watertight connection between portable transmitting unit 238 and cover 286. Connector 236b typically includes pogo pins such as pogo pin 302 received in a port of connector 236a or otherwise disposed to contact a trace or pad associated with connector 236a or conductive element 291 as shown.

Figure 18:
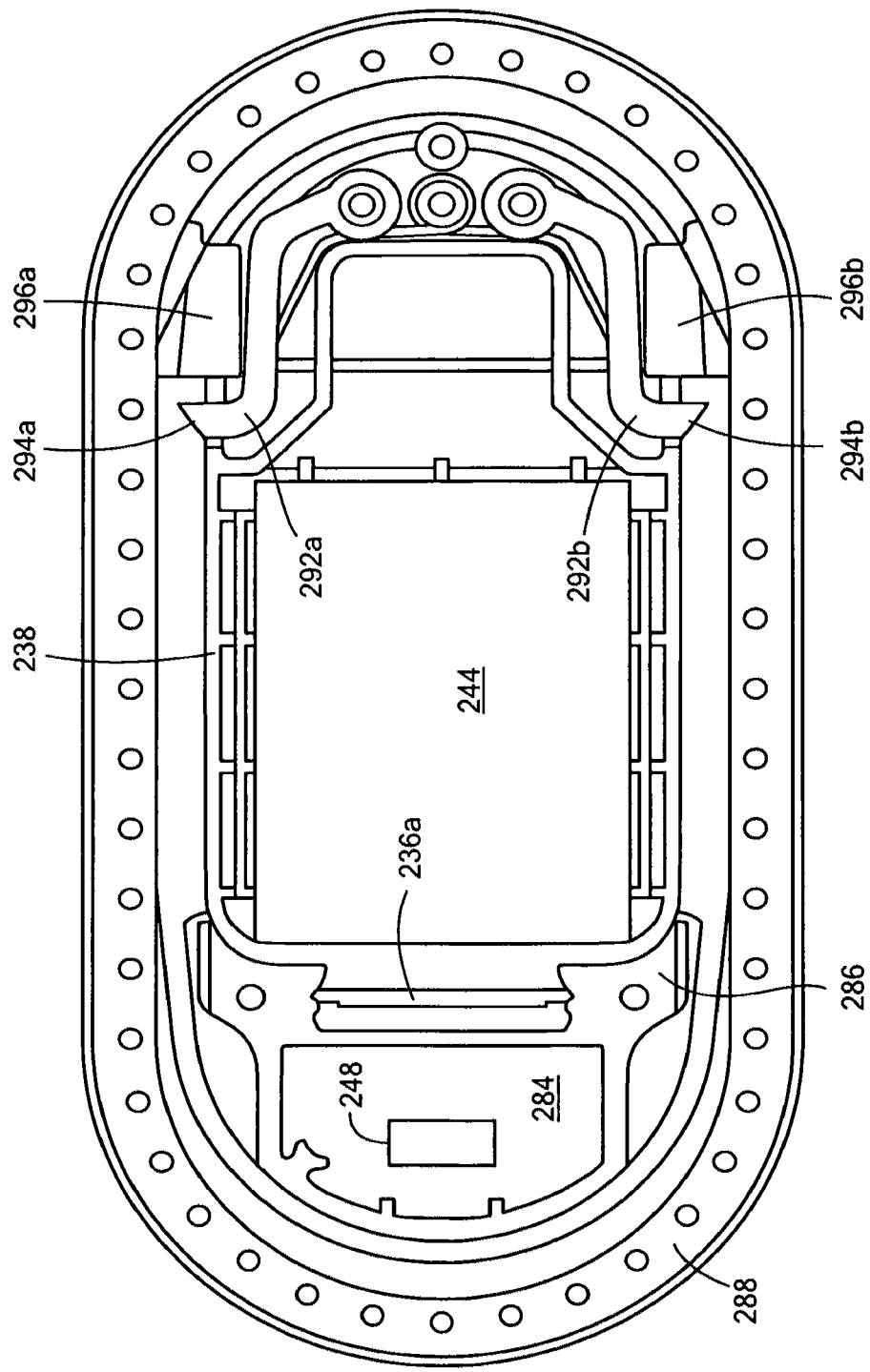
FIG. 18 is a schematic cross-sectional top view of the subassembly shown in FIG. 17.

FIGS. 17 and 18 also show portable transmitting unit 238 antenna 242, power supply (e.g., a lithium battery) 244, and main printed circuit board 310 (for controlling electronics 246 and transmitter 240, FIG. 11). Included may be a microprocessor for processing signals from the accelerometer, respirator, heart rate sensor, and any other sensors for transmission by the transmitter of portable transmitting unit 238. Double sided tape 241 may be placed between antenna 242 and printed circuit board 310. Transmitter 240 is also shown in FIG. 17 as is accelerometer 248. PCB 310 acts as a ground plane for the antenna and decouples the wearer's body from RF energy transmitted via antenna 242 increasing the transmission range. Battery 244 is behind antenna 242 so no RF energy is blocked. Preferably, no conductive components block antenna 242.

In accordance with one aspect of the subject invention, a new physiological monitoring system is provided which, in one specific version, is more ergonomic than prior systems. Various other embodiments are within the scope of the subject invention.

The subject invention features, in one example, a physiological monitoring system comprising a garment such as a shirt, a band integrated with the garment including respiration sensing conductors and one or more additional conductors, and a heart rate sensor integral with the garment electrically connected to an additional conductor. A dock is attached to the garment and includes a receptacle comprising a printed circuit board including an accelerometer and a first connector component electrically connected to said respiration sensing conductors and the additional conductor(s) and a cover over said printed circuit board. A housing is attached to the garment and receives the receptacle therein. A portable transmitting unit is removeably received in the dock and includes a second connector component mateable with the first connector component. The portable transmitting unit is configured to wirelessly transmit respiration, heart rate, and accelerometer data to a base unit.

Padding may be included behind the receptacle and/or over the housing for comfort. Preferably, the housing has a concave shape. Fasteners may secure the receptacle inside the housing. One preferred housing includes a tongue member and side rails upstanding therefrom receiving the portable transmitting unit therebetween. Typically, the rails curve inwardly over the tongue member. Also, the portable transmitting unit may include a latch mechanism releasably engaging the portable transmitting unit in the housing. The latch mechanism may include spaced spring loaded fingers releasably received in indentations in the housing.

In one version, the dock with the portable transmitting unit received therein is no larger than 8 inches wide, 4 inches long, and 3 inches high.

The second connector component may include pogo pins and then the first connector component includes conductors for the pogo pins. A seal member may be included about the first connector component. Typically, the cover is sewn and/or glued to the band. A typical portable transmitting unit further includes a printed circuit board, a battery under the printed circuit board, and an antenna over the printed circuit board acting as a ground plane for the antenna.

The subject invention also features a physiological monitoring system comprising a sensor subsystem worn by a person including at least a heart rate sensor, a dock associated with the sensor subsystem including a first connector component electrically connected to the heart rate sensor, and a portable transmitting unit received in the dock including a transmitter and a connector component removeably mateable with the dock connector component to route heart rate data to the transmitter. The preferred sensor subsystem includes a flexible band integrated with a shirt including at least one conductor extending between the heart rate sensor and the dock. The band may include a pair of conductors configured for sensing respiration.

One typical physiological monitoring system in accordance with the subject invention features a sensor subsystem worn by a person including at least one sensor (e.g., a heart rate sensor). A dock is associated with the sensor subsystem and includes a receptacle comprising a printed circuit board including a dock connector component electrically connected to the sensor and a cover over the printed circuit board, and a housing receiving the receptacle therein. A portable transmitting unit is received in the dock and includes a transmitter and a connector component removeably mateable with the dock connector component to route sensor data to the transmitter.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A load score system comprising:
    a metabolic sensor for a subject configured to output metabolic data for the subject;
    a biomechanical load sensing subsystem for the subject configured to output biomechanical load data;
    a speed sensor subsystem for the subject configured to output speed data;
    one or more databases storing zones and a weighting factor for each zone for metabolic data, biomechanical load data, and speed data;
    a performance module responsive to the metabolic data, the biomechanical load data, and the speed data and the one or more data bases and configured to:
    calculate a metabolic load score for the subject,
    calculate a biomechanical load score for the subject, and
    calculate a speed load score for the subject; and
    an output module configured to display the subject's calculated metabolic, biomechanical, and speed load scores.

2. The system of claim 1 in which the biomechanical load sensing subsystem and the speed sensor subsystem include an accelerometer.

3. The system of claim 2 in which the accelerometer is a three axis accelerometer.

4. The system of claim 3 in which biomechanical load sensing subsystem includes means for processing the outputs of the three axis accelerometer.

5. The system of claim 3 in which the speed sensor subsystem includes means for processing one output of the three axis accelerometer.

6. The system of claim 1 in which the performance module is configured to detect peaks in the biomechanical load data above a threshold, detect events based on the peaks, and for each event determine a zone for and a weighting factor to be applied to biomechanical load data to output a biomechanical load score for the subject.

7. The system of claim 1 in which speed sensor subsystem is configured to identify steps and their frequency to determine speed data.

8. The system of claim 7 in which the performance module is configured to determine a zone for and a weighting factor to be applied to the speed data to output a speed load score for the subject.

9. The system of claim 1 in which the performance module is configured to determine a zone for and a weighting factor to be applied to the metabolic data to output a metabolic load score for the subject.

10. The system of claim 1 in which the metabolic sensor is a heart rate sensor.

11. The system of claim 1 in which the performance module includes a clustering function configured to increase a said load score by a predetermined factor if a predetermined number of load events occur within a predetermined time period.

12. The system of claim 1 further including:
a garment;
a band integrated with the garment including respiration sensing conductors and one or more additional conductors connected to a heart rate sensor;
a dock attached to the garment, the dock including:
a receptacle comprising:
a cover secured to the band,
a printed circuit board associated with the cover and including an accelerometer for the biomechanical load sensing subsystem and the speed sensor subsystem and a first connector component electrically connected to said respiration sensing conductors and said at least one additional conductor;
a housing attached to the garment and receiving the receptacle therein; and
a portable transmitting unit removeably received in the dock and including a second connector component mateable with the first connector component.

13. The load score system of claim 1 in which the performance module is further configured to determine a total load score based on the metabolic load score, the speed load score, and the biomechanical load score.

14. A physiological monitoring method comprising:
determining heart rate data of a person, the person's speed data, and a biomechanical load data experienced by the person;
establishing a set of zones for metabolic load, speed load, and biomechanical load, each zone having an upper threshold, a lower threshold, and a weighting factor;
based on the determined heart rate data, determining the time spent in each metabolic load zone and multiplying the weighting factor for each load zone by the time spent in each zone to determine a metabolic load score;
based on the speed data, allocating the determined speed data amongst the various speed zones based on the thresholds for each said zone and applying the weighting factor for each said zone to determine a speed load score; and
based on the biomechanical load data, allocating the determined biomechanical load data amongst the various biomechanical load zones based on the threshold for each said zone and applying the weighting factor for each said zone to determine a biomechanical load score.

15. The method of claim 14 further including the step of determining a total load score based on the metabolic load score, the speed load score, and the biomechanical load score.

16. A physiological monitoring system comprising:
a metabolic sensor configured to output metabolic data for a subject;
a biomechanical load sensing subsystem for the subject configured to determine a biomechanical load event;
a speed sensor subsystem for the subject configured to determine a step event and to calculate speed data based on step events and the time between step events;
one or more databases storing zones and a weighting factor for each zone for metabolic data, biomechanical load, and speed data; and
a performance module responsive to the metabolic data, biomechanical load, and speed data and the one or more databases and configured to:
calculate a metabolic load score for the subject by determining, for said metabolic data, a zone for the metabolic data and a weighting factor for the metabolic data and, based on the zone and weighting factor, to determine a metabolic load score,
calculate a speed load score for the subject by determining, for said speed data, a zone for the speed data and a weighting factor for the speed data, and based on the zone and weighting factor, to determine the speed load score, and
calculate a biomechanical load score for the subject by determining, for a said biomechanical load event, a zone for said biomechanical load event and a weighting factor for the biomechanical load event, and based on said zone and said weighting factor, to determine a biomechanical load score.

17. The system of claim 16 in which the biomechanical load sensing subsystem and the speed sensor subsystem include an accelerometer.

18. The system of claim 17 in which the accelerometer is a three axis accelerometer.

19. The system of claim 18 in which biomechanical load sensing subsystem includes means for processing the outputs of the three axis accelerometer.

20. The system of claim 18 in which the speed sensor subsystem includes means for processing one output of the three axis accelerometer.

21. The system of claim 16 in which the performance module is configured to detect peaks in the biomechanical load data above a threshold, detect biomechanical load events based on the peaks, and for each biomechanical event, determine a zone for and a weighting factor to be applied to output a biomechanical load score for the subject.

22. The system of claim 16 in which speed sensor subsystem is configured to identify steps and their frequency to determine speed data.

23. The system of claim 22 in which the performance module is configured to determine a zone for and a weighting factor to be applied to the speed data to output a speed load score for the subject.

24. The system of claim 16 in which the performance module is configured to determine a zone for and a weighting factor to be applied to the metabolic data to output a metabolic load score for the subject.

25. The system of claim 16 in which the metabolic sensor is a heart rate sensor.

26. The system of claim 16 in which the performance module includes a clustering function configured to increase a said load score by a predetermined factor if a predetermined number of load events occur within a predetermined time period.

27. A load score system comprising:
a metabolic sensor for a subject configured to output metabolic data for the subject;
a biomechanical load sensing subsystem for the subject configured to output biomechanical load data;
a speed sensor subsystem for the subject configured to output speed data;
one or more databases storing zones and a weighting factor for each zone for metabolic data, biomechanical load data, and speed data;
a performance module responsive to the metabolic data, the biomechanical load data, and the speed data and the one or more data bases and configured to:
calculate a metabolic load score for the subject,
calculate a biomechanical load score for the subject, and
calculate a speed load score for the subject; and
an output module configured to display the subject's calculated metabolic, biomechanical, and speed load scores; and further including:
a garment;
a band integrated with the garment including respiration sensing conductors and one or more additional conductors connected to a heart rate sensor;
a dock attached to the garment, the dock including:
a receptacle comprising:
a cover secured to the band,
a printed circuit board associated with the cover and including an accelerometer for the biomechanical load sensing subsystem and the speed sensor subsystem and a first connector component electrically connected to said respiration sensing conductors and said at least one additional conductor;
a housing attached to the garment and receiving the receptacle therein; and
a portable transmitting unit removeably received in the dock and including a second connector component mateable with the first connector component.

\* \* \* \* \*